(12) United States Patent
Mani et al.

(10) Patent No.: US 11,426,526 B2
(45) Date of Patent: Aug. 30, 2022

(54) DISPENSING DEVICE

(71) Applicant: Tata Elxsi Limited, Bangalore (IN)

(72) Inventors: Vasanthan Mani, Bangalore (IN); Suresh Kumar Natarajan, Bangalore (IN)

(73) Assignee: Tata Elxsi Limited, Bangalore (IN)

(*) Notice: Subject to any disclaimer, the term of this patent is extended or adjusted under 35 U.S.C. 154(b) by 333 days.

(21) Appl. No.: 16/485,107

(22) PCT Filed: Feb. 5, 2018

(86) PCT No.: PCT/IB2018/050699
§ 371 (c)(1),
(2) Date: Aug. 9, 2019

(87) PCT Pub. No.: WO2018/146589
PCT Pub. Date: Aug. 16, 2018

(65) Prior Publication Data
US 2019/0374725 A1     Dec. 12, 2019

(30) Foreign Application Priority Data

Feb. 13, 2017   (IN) .............................. 201741005073

(51) Int. Cl.
A61M 5/315     (2006.01)

(52) U.S. Cl.
CPC .... A61M 5/31555 (2013.01); A61M 5/31585 (2013.01); A61M 5/31501 (2013.01);
(Continued)

(58) Field of Classification Search
CPC .......... A61M 5/31555; A61M 5/31585; A61M 5/31501; A61M 5/31511; A61M 5/31595; A61M 5/50; A61M 2205/273
See application file for complete search history.

(56) References Cited

U.S. PATENT DOCUMENTS 5,009,645 A    4/1991   Silver et al.
5,582,598 A    12/1996  Chanoch
(Continued)

FOREIGN PATENT DOCUMENTS

EP       2579925 A1       4/2013
WO    WO2011154481 A1   12/2011
WO    WO 2016/050902    4/2016

OTHER PUBLICATIONS

International Search Report dated Aug. 21, 2018, in corresponding International Application No. PCT/IB2018/050699; 7 pages.
(Continued)

*Primary Examiner* — Shefali D Patel
(74) *Attorney, Agent, or Firm* — Finnegan, Henderson, Farabow, Garrett & Dunner, L.L.P.

(57) ABSTRACT

A dispensing device is provided to dispense a designated amount of a material on every dose delivery operation. The dispensing device includes a thumb pad, a cam drum coupled to the thumb pad, and a pawl nut comprising a one-way pawl. The thumb pad may be pulled out in a direction away from a distal end of the dispensing device for setting a dose of the material to be dispensed out and may be pushed in towards the distal end for delivering the dose. The cam drum includes a plurality of linear cam profiles and a plurality of helical cam profiles that may be disposed on a surface of the cam drum. The one-way pawl may engage with a ratchet disposed at a distal end of the cam drum and may prevent a rotation of the cam drum in an undesired direction.

30 Claims, 15 Drawing Sheets

(52) U.S. Cl.
CPC ..... *A61M 5/31511* (2013.01); *A61M 5/31595* (2013.01); *A61M 2205/273* (2013.01)

(56) References Cited

U.S. PATENT DOCUMENTS

| | | |
|---|---|---|
| 7,695,454 B2 | 4/2010 | Barron et al. |
| 8,992,484 B2 | 3/2015 | Radmer et al. |
| 2002/0004648 A1 | 1/2002 | Larsen et al. |
| 2009/0240195 A1 | 9/2009 | Schrul et al. |
| 2010/0137792 A1 | 6/2010 | Boyd et al. |
| 2011/0196339 A1 | 8/2011 | Hirschel et al. |
| 2012/0310168 A1 | 12/2012 | Plumptre et al. |
| 2012/0310206 A1* | 12/2012 | Kouyoumjian ... A61M 5/31585 604/506 |
| 2013/0150799 A1* | 6/2013 | Radmer ............ A61M 5/31528 604/189 |
| 2015/0094687 A1 | 4/2015 | Boyd et al. |

OTHER PUBLICATIONS

Written Opinion dated Aug. 21, 2018, in corresponding International Application No. PCT/IB2018/050699; 8 pages.

* cited by examiner

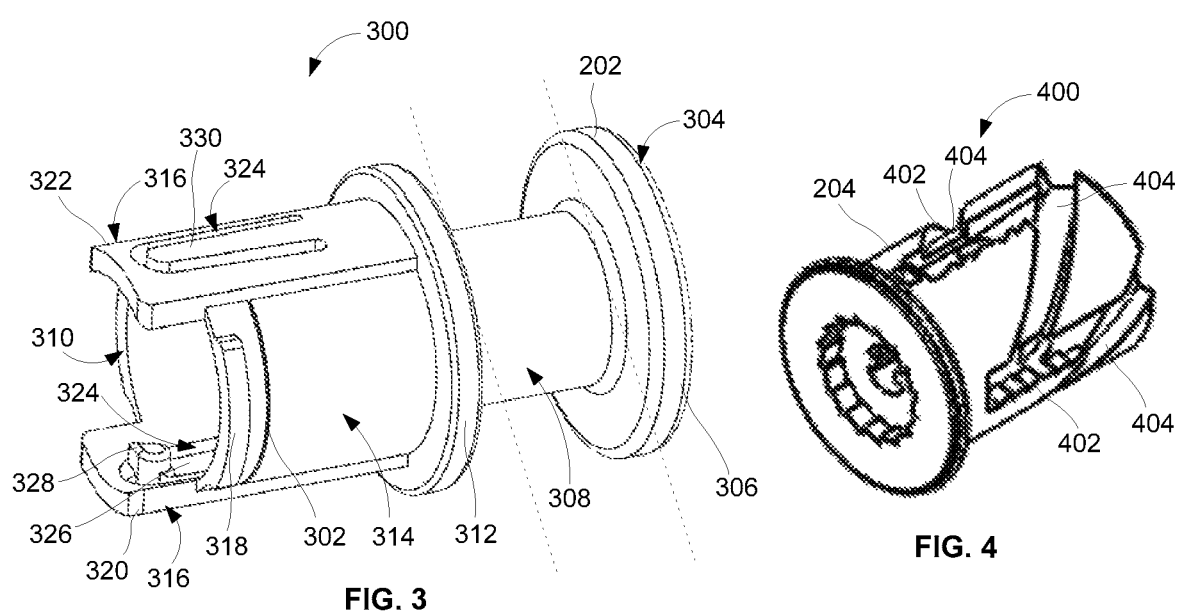

DISPENSING DEVICE

CROSS-REFERENCE TO RELATED PATENT APPLICATIONS

This application is a national stage application of International Application No. PCT/IB2018/050699, filed Feb. 5, 2018, which claims priority to Indian Application No. 201741005073, filed Feb. 13, 2017, each of which is hereby incorporated by reference in its entirety.

BACKGROUND

Embodiments of the present specification relate generally to a dispensing device, and more particularly to a dispensing device that is adapted to deliver the same amount of substance upon every single actuation of the dispensing device.

Generally, treating patients suffering from various diseases entails injecting medication substances using syringe devices. One example of a simple syringe device includes a transparent medication barrel that includes graded scale markings marked on a cylindrical external surface of the transparent medication barrel. The graded scale markings allow a caregiver to set a desired dose to be injected into a patient's body. A proximal end of the transparent medication barrel includes a plunger, and a stopper that is placed within the medication barrel and is coupled to one end of the plunger. A distal end of the transparent medication barrel is designed and is shaped to couple to a needle that pierces patient's skin for injecting a medication substance by actuating the plunger.

The amount of substance to be injected is set by piercing the needle through a rubber stopper of a container carrying a medication substance and by pulling out the plunger towards the distal end. The plunger is pulled out towards the distal end until level of the medication substance within the medication barrel corresponds to a desired graded scale marking. Then, the syringe device is primed to remove any air bubbles that may be formed while setting the dose and is ensured that the syringe device is carrying only the desired amount of medication substance to be injected. Then, the set dose is injected by pushing the plunger towards the proximal end, during which time, the plunger along with the stopper moves within the transparent medication barrel. Movement of the plunger and stopper within the transparent medication barrel causes the enclosed medicament substance to pass out through the needle.

When treating certain diseases, the treatment may require the same amount of substance to be injected once in a week, once in a day, or at designated intervals in the day. For such cases, injector pens have been developed that allow patients to set and deliver a dose themselves more accurately in a controlled manner. Such injector pens, in general, have a cartridge that contains a rubber stopper and a multi-dose quantity of medication substance. In addition, from a distal end of such typical injection pens, a driving member extends out within its base and operably connects to mechanisms at a distal end of the pen. While delivering a fixed dose, the mechanisms control the movement of the driving member towards the distal end of the pen. Thus, the driving member with its controlled movement pushes the rubber stopper to dispense only a designated amount of medication substance from the cartridge.

Once a final dose is delivered and the cartridge is empty, most often, the injector pens are designed such that the patients would not be able to re-use the injector pens. Mechanisms that prevent re-using of the injector pens are in-built into the injector pens to avoid risks associated with re-using of the injector pens such as microbial growth and contamination at the needle tip, experiencing pain when injecting the medication substance, breaking off the needle, formation of lumps on the skin, etc. However, the existing injector pens that are capable of injecting the same amount of substance multiple times are costlier, use complex mechanisms and expensive components to set the dose, to deliver the set dose, and to prevent re-using of the pens after their end of life (EOL). Accordingly, there remains a need for a dispensing device that has in-built mechanisms that execute all the functionalities of the typical injector pens, but is still cost-effective, more efficient, has improved accuracy in setting and delivering the dose, and prevents re-using of the dispensing device after its EOL.

BRIEF DESCRIPTION

According to an exemplary aspect of the present specification, a dispensing device is provided. The dispensing device includes a thumb pad and a cam drum. The thumb pad is configured to be pulled out towards a proximal end of the dispensing device for setting a dose of a material to be dispensed out and to be pushed in towards a distal end of the dispensing device for delivering the dose. The cam drum that is coupled to the thumb pad. The cam drum includes at least one linear cam profile and at least one helical cam profile that are disposed on a surface on the cam drum. The thumb pad is configured to ride on the least one linear cam profile when setting the dose and is further configured to ride on the at least one helical cam profile when delivering the dose.

The cam drum may include a selected number of linear cam profiles and the selected number of helical cam profiles. Each of the linear cam profiles may include a start point, an end point, a one-way ratchet extending between the start point and the end point, and a slot that is located in a path of each of the linear cam profiles. Each of the helical cam profiles may include a corresponding start point and an end point. A helical cam profile selected from the helical cam profiles is located subsequent to every end point of a linear cam profile selected from the linear cam profiles. The linear cam profile is located subsequent to every end point of the helical cam profile.

Each of the linear cam profiles may define a gradient path having a slope that gradually increases from the start point to the end point associated with each of the linear cam profiles. Each of the helical cam profiles may define a gradient path having a slope that gradually increases from the start point to the end point associated with each of the helical cam profiles. The thumb pad may include a visual indicator, an intermediate portion, a butting surface, and a circular shaped hollow body. The visual indicator is externally visible when the thumb pad is pulled out towards the proximal end by a designated distance to indicate the completion of a dose setting process. The intermediate portion is a hollow elongated body. The circular shaped hollow body may include a first extension, a second extension, and one or more snap locks. The first extension and the second extension may extend out from the butting surface 312.

The first extension may include a first lever and a U-shaped slot on a surface of the first extension. The second extension may include a second lever and another U-shaped slot on a surface of the second extension. The first lever may include a first pawl and the second lever may include a second pawl. The dispensing device may further include a plurality of ribs, a one-way pawl, and a slot. The one-way pawl may be configured to engage with a ratchet that is disposed at a distal end of the cam drum and is further configured to prevent a rotation of the cam drum in an undesired direction. The slot may include a threaded section that includes a designated pitch.

A lead screw of the dispensing device may include a flange, a body that comprises a thread portion, and a universal ball joint that is configured to be secured to a push pad of the dispensing device. The thread portion may include a designated pitch that corresponds to the designated pitch of the pawl nut. The cam drum may further include a keyway that is disposed at a proximal end of the cam drum. The lead screw may be configured to pass through the keyway and is coupled to the cam drum. At an initial state of the dispensing device before setting a first dose, the thumb pad is coupled to the cam drum such that the first lever having the first pawl is configured to be placed at a start point of a linear cam profile of the cam drum. The second lever having the second pawl is configured to be placed at a start point of another linear cam profile of the cam drum. The linear cam profile that corresponds to the first lever may be different from the linear cam profile that corresponds to the second lever.

The first lever having the first pawl may be configured to move linearly from the start point of the linear cam profile and to ride on a one-way ratchet of the linear cam profile. Simultaneously, the second lever having the second pawl may be configured to move linearly from the start point of the another linear cam profile and to ride on a one-way ratchet of the another linear cam profile when the dose is set by pulling out the thumb pad towards the proximal end. The first pawl and the second pawl are configured to be locked with the corresponding one-way ratchet, and thereby prevent a linear motion of the thumb pad towards the distal end when delivery of the dose is attempted without pulling out the thumb pad by the designated distance towards the proximal end.

The first lever may be configured to complete a gradient path defined by the linear cam profile and be placed at a ready position at a start point of a helical cam profile. Simultaneously, the second lever may be configured to complete a gradient path defined by the another linear cam profile and be placed at a ready position at a start point of another helical cam profile at an end of a dose setting stage. The helical cam profile on which the first lever is positioned is different from the helical cam profile on which the second lever is positioned. Each of the first lever and the second lever may be configured to ride on a gradient path defined by the corresponding helical cam profile when the dose is delivered by pushing the thumb pad linearly towards the distal end after the dose is set by pulling out the thumb pad by the designated distance.

The first and second levers may be configured to push and rotate the cam drum in a desired direction when the first lever and the second lever ride on the corresponding helical cam profile, thereby converting a linear motion of the thumb pad towards the distal end into a circular motion of the cam drum in the desired direction. The cam drum may be configured to complete one rotation at a desired angle in the desired direction when the first lever and the second lever complete the gradient path defined by the corresponding helical cam profile. The lead screw may be configured to rotate along with the cam drum in the desired direction as the lead screw is locked with the cam drum through the keyway when delivering the dose. The designated pitch associated with the lead screw may correspond to the designated pitch associated with the threaded section of the pawl nut, thereby configuring the pawl nut to convert a circular motion of the lead screw into a linear motion towards the distal end by a desired distance. The lead screw that is moved by the desired distance pushes a stopper within a cartridge to dispense the dose from the cartridge.

The dispensing device may be configured to deliver a fixed dose on every single dose delivery operation of the dispensing device. Each of the first and second levers is configured to ride on the gradient path defined by the corresponding helical cam profile to rotate the cam drum by the designated angle. In addition, thereby configuring the lead screw to rotate and move further from a current position every time by a same distance to dispense the fixed dose during every dose delivery operation. A length of the lead screw may be selected such that when the cam drum completes one rotation, the lead screw is configured to rotate and move by a distance that causes the entire dose accommodated within the cartridge to dispense out in a single dose delivery operation. The cam drum may further include a barrel engaging surface and one or more guide ribs. The one or more guide ribs are configured to guide the lead screw to pass through the keyway when the cam drum rotates during delivering the dose.

A pen barrel of the dispensing device acts as an outer body component that is coupled to the butting surface of the thumb pad. The pen barrel may include a circular rib, one or more semi-circular ribs, one or more depressions, one or more slots, a first pair of guiding surfaces, and a second pair of guiding surfaces. The circular rib secured to the barrel engaging surface of the cam drum so as to prevent a linear motion of the cam drum towards the proximal end when setting the dose, and prevent a linear motion of the cam drum towards the distal end when delivering the dose. Each of the one or more semi-circular ribs may be configured to be locked with the thumb pad to prevent the thumb pad from moving further towards the proximal end when the thumb pad is pulled out towards the proximal end by the designated distance.

The one or more depressions may be disposed at inner surfaces of the pen barrel to provide adequate spaces for the first lever and the second lever to flex up and down and to ride smoothly on linear cam profiles and helical cam profiles of the cam drum. Each of the one or more slots may be configured to receive and accommodate a rib of the pawl nut such that the pawl nut is placed in a locked condition with respect to the pen barrel. The first extension of the thumb pad fits within and engages against the first pair of guiding surfaces. The second extension of the thumb pad fits within and engages against the second pair of guiding surfaces. The first and second pair of guiding surfaces may guide the first and second extensions, respectively, in a linear fashion in order to move the thumb pad linearly without undergoing a circulatory motion when the thumb pad is pulled out towards the proximal end or when the thumb pad is pushed in towards the distal end.

In another aspect, a dispensing device is provided. The dispensing device includes a cam drum, a thumb pad, a lead screw, a plurality of end of life (EOL) locks, and an end of life (EOL) adapter. The thumb pad is coupled to the cam drum and is configured to set and deliver a dose of a material to be dispensed out. The lead screw includes a flange and the lead screw is placed at a first position within the thumb pad at an initial state of the dispensing device. The lead screw is configured to rotate along with the cam drum and move by a designated distance during every dose delivery operation to deliver a fixed dose. Each of the one or more EOL locks includes an elastic member seating surface, a flange-engaging portion, and an elevated portion. The EOL adapter acts as a carrier of the EOL locks and the EOL adapter is coupled to the cam drum. The flange of the lead screw is configured to be positioned below flange engaging portions of the EOL locks that prevent the thumb pad from moving further towards a proximal end to prevent further setting of the dose after a final dose is delivered.

The EOL adapter may include a plurality of portions and at least one snap lock feature for locking the EOL adapter with the cam drum. Each of the plurality of portions of the EOL adapter includes a first flexure, a second flexure, an EOL lock seating surface that is disposed between the first flexure and the second flexure, and a peg that protrudes out from the EOL locking seating surface. The dispensing device may further include one or more elastic members. Each peg associated with the EOL adapter supports an elastic member. Each of the EOL locks may be coupled to the EOL adapter by seating an elastic member seating surface corresponding to an EOL lock on an elastic member that is supported by a peg of the EOL adapter.

The EOL adapter along with the EOL locks may be placed within the cam drum and may be locked with the cam drum using the at least one snap lock feature. One or more elevated portions associated with the EOL locks protrude out through slots disposed along one or more paths defined by one or more linear cam profiles of the cam drum when the EOL adapter is locked with the cam drum. Pawls associated with the thumb pad ride over the linear cam profiles and compress the elevated portions associated with the EOL locks within the cam drum to move further and complete a dose setting process when the dose is set by pulling out the thumb pad towards the proximal end of the dispensing device.

The flange of the lead screw is configured to be positioned within the cam drum and below the flange engaging portions of the EOL locks after the final dose is delivered. The elevated portions may be prevented from undergoing compression within the cam drum due to the presence of the flange causing a block in a path of the thumb pad to prevent setting of another dose subsequent to delivery of the final dose.

BRIEF DESCRIPTION OF DRAWINGS

These and other features, aspects, and advantages of the claimed subject matter will become better understood when the following detailed description is read with reference to the accompanying drawings in which like characters represent like parts throughout the drawings, wherein:

FIG. 3 illustrates a side perspective view of a thumb pad depicted in FIG. 2;

FIG. 4 illustrates a front perspective view of a cam drum depicted in FIG. 2;

DETAILED DESCRIPTION

The following description presents an exemplary dispensing device that is configured to dispense a fixed amount of material (e.g., a medicament) upon every single injection operation. To that end, various components are provided in the dispensing device that allow a user to set a dose of a material to be dispensed, deliver the dose, prevent a user from setting a wrong dose, and prevent a user from setting the dose after a final dose (EOL) is delivered. The term "dose," used in the various embodiments described herein, broadly refers to an amount of a material to be dispensed. Examples of the material include a medicament, a chemical substance, and a composition of substances. Certain exemplary configurations of the dispensing device that provide the various features and functions defined herein are described in greater detail with reference to FIGS. 1-33.

Figure 1:
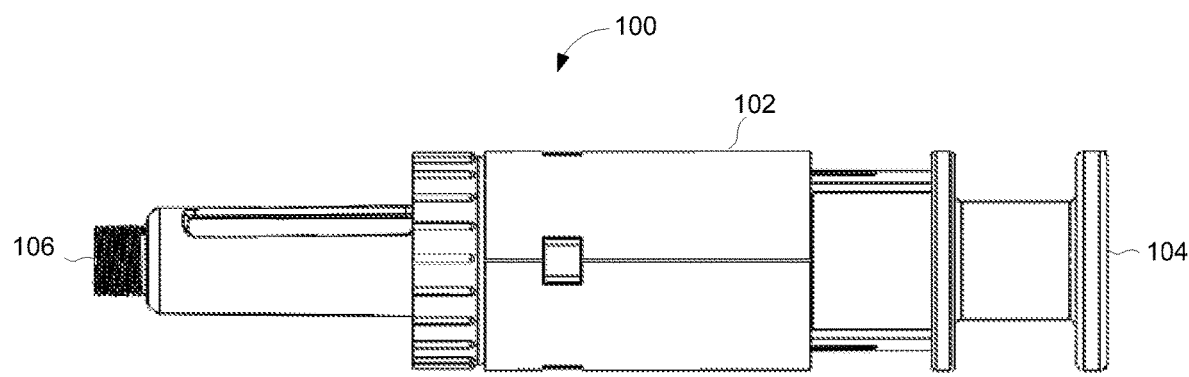
FIG. 1 illustrates a top view of a dispensing device, according to one embodiment of the present disclosure.

FIG. 1 illustrates a top view (100) of an exemplary dispensing device (102). In one embodiment, the dispensing device (102) is a medication-dispensing device having an appearance of a pen. In certain embodiments, the dispensing device (102) is a disposable device that is repeatedly operable by a user to deliver a fixed dose of the medication. The term "fixed dose," used herein and throughout various embodiments, broadly refers to substantially the same amount of substance delivered through a needle on every single actuation of the dispensing device (102). The dispensing device (102) includes a proximal end (104) including an actuation mechanism and a distal end (106) for securing the needle that delivers the fixed dose of medication to a patient. Various components of the dispensing device (102) are depicted and described in greater detail with reference to FIGS. 2 through 25.

Figure 2:
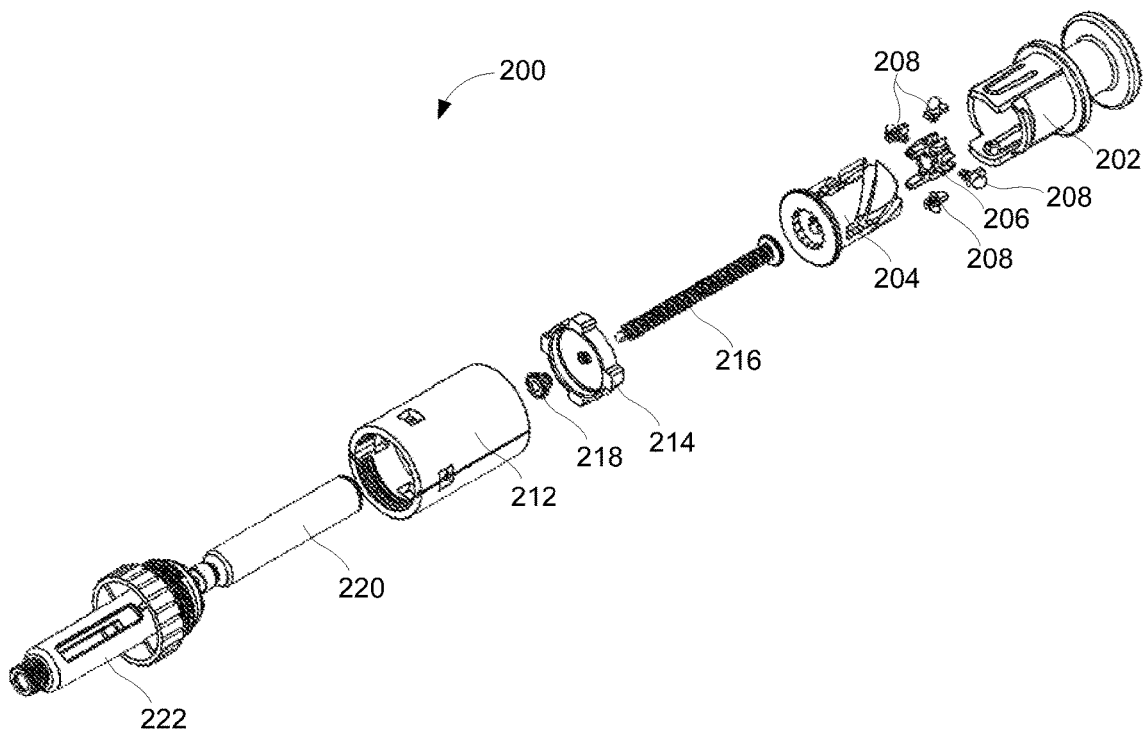
FIG. 2 is an exploded view of the dispensing device of FIG. 1, according to one embodiment of the present disclosure.

FIG. 2 is an exploded view (200) of the dispensing device (102) of FIG. 1, according to one embodiment of the present disclosure. The dispensing device (102) includes a thumb pad (202), a cam drum (204), an end of life (EOL) adapter (206), one or more end of life (EOL) locks (208), one or more end of life (EOL) elastic members (210) (shown in FIG. 15), a pen barrel (212), a pawl nut (214), a lead screw (216), and a push pad (218). The dispensing device (102) further includes a cartridge (220), a cartridge holder (222), and a needle (not shown in FIG. 2) having a needle hub for securing the needle to the cartridge holder (222). Each of these components of the dispensing device (102) is depicted and described in detail in subsequent figures and paragraphs.

FIG. 3 illustrates a side perspective view (300) of the thumb pad (202) of FIG. 2, according to one embodiment of the present disclosure. In one embodiment, the thumb pad (202) is a circular shaped body that is used for setting a dose and for delivering the dose. For setting a dose, the thumb pad (202) is pulled out in a direction of the proximal end (104) of the dispensing device (102). In certain embodiments, the thumb pad (202) includes an identification groove (302) that is visible to a user when the thumb pad (202) is completely pulled out and is disposed in a ready position to deliver the dose to visually indicate to a user that the dose has been set. In one embodiment, instead of the identification groove (302), the thumb pad (202) can have other indication mechanisms (e.g., a color indication) to notify the user that the dose has been set. For delivering the dose, the thumb pad (202) is pushed in the direction of the distal end (106) of the dispensing device (102).

In certain embodiments, a proximal portion (304) of the thumb pad (202) includes a holding surface (306) (depicted as an annulus-shaped portion in FIG. 3) that allows the user to hold the thumb pad (202) and to actuate the thumb pad (202) for setting and delivering the dose. The thumb pad (202) further includes an intermediate portion (308) disposed between the proximal portion (304) and a distal portion 310. The intermediate portion (308) is a hollow elongated body having an interior space for accommodating the lead screw (216). The distal portion (310) includes a butting surface (312), and a circular shaped hollow body (314) having extensions (316) and snaps locks 318.

The butting surface (312) acts a forward stopper. The butting surface (312) engages against a surface of the pen barrel (212) and prevents the thumb pad (202) from moving further in the direction of the distal end (106) after the dose is delivered. The snap locks (318) act as reverse stoppers. The snap locks (318) enable the thumb pad (202) to lock with semi-circular ribs (shown in FIG. 17) of the pen barrel (212) upon completely pulling out the thumb pad (202) in the direction of the proximal end (104) and prevent the thumb pad (202) from moving further. In one embodiment, the thumb pad (202) is configured to move linearly without rotation while setting and delivering the dose to prevent unnecessary rotation of the cam drum (204). To that end, the extensions (316) of the thumb pad (202) are configured to fit within and slide against guiding surfaces (shown in FIG. 17) of the pen barrel (212). The guiding surfaces of the pen barrel (212) act as guiding rails for the extensions (316) and enable a linear motion of the thumb pad (202). In one embodiment, the thumb pad (202) is configured to execute various functionalities such as setting doses and delivering the set doses. The thumb pad (202) is designed in a way such that the thumb pad (202) rides on linear cam profiles (shown and described in FIG. 4) of the cam drum (204) while setting the doses. While delivering the set doses, the thumb pad (202) rides on helical cam profiles (shown and described in FIG. 4) of the cam drum (204).

In one embodiment, the extensions (316) include a first extension (320) and a second extension (322) extending out from the butting surface 312. Each of the first extension (320) and the second extension (322) includes a U-shaped cut portion (324) on its surface and a lever disposed between the U-shaped cut portion 324. More particularly, the first extension (320) includes a first lever (326) having a pawl 328. Similarly, the second extension (322) includes a second lever (330) having a pawl (332) (shown in FIG. 27). The first lever (326) and the second lever (330) are configured to flex up and down to ride on a linear cam profile and a helical cam profile of the cam drum (204) during dose setting and dose delivery stages. In addition, the first lever (326) and the second lever (330) are also configured to flex right and left to ride on the ratchet cam profile during dose setting, as described in detail with reference to FIGS. 4 through 8.

FIG. 4 illustrates a front perspective view (400) of the cam drum (204) of FIG. 2, according to one embodiment of the present disclosure. The cam drum (204) is configured to execute various significant functionalities in the dispensing device (102). Firstly, while setting the dose, the thumb pad (202) is to be fully pulled out in the direction of the proximal end (104) until the identification groove (204) is visible to the user. If the user does not fully pull out the thumb pad (202) and tries to inject a medication by mistake, the cam drum (204) ensures that the thumb pad (202) does not move forward while attempting to inject the medication, and hence, the dose would not be delivered. Secondly, while delivering the dose, the cam drum (204) transfers a linear motion of the thumb pad (202) in the direction of the distal end (106) into a circular motion of the lead screw (216) by its own rotation and using the pawl nut (214). At every dose delivery, the cam drum (204) is rotated by a designated angle (e.g., 90 degrees) causing the lead screw (216) to move by a designated distance, which leads to delivery of the fixed dose every time.

To that end, the cam drum (204) is provided with a plurality of linear cam profiles (402) and a plurality of helical cam profiles (404). The linear cam profiles and the helical cam profiles are disposed on a desired surface of the cam drum (204). As used herein, the term "linear cam profile" and variations thereof refer to paths through which the levers (326) and (330) of the thumb pad (202) may ride while setting a dose. The term "helical cam profiles," used herein, refers to paths through which the levers (326) and (330) of the thumb pad (202) may ride while delivering a dose. In certain embodiments, the cam drum (204) includes four linear cam profiles and four helical cam profiles, as described with reference to FIG. 5. However, it is to be understood that the cam drum (204) can have any such number of linear cam profiles (402) and helical cam profiles (404).

Figure 5:
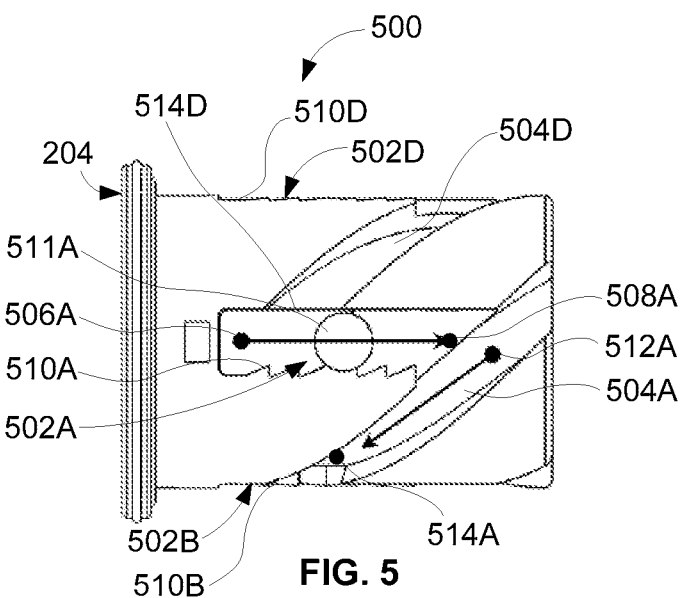
FIG. 5 illustrates a front view of the cam drum depicted in FIG. 2.

FIG. 5 illustrates a front view (500) of the cam drum (204) of FIG. 2, according to one embodiment of the present disclosure. In one exemplary embodiment, the cam drum (204) may have four linear cam profiles including a first linear cam profile (502A), a second linear cam profile (502B), a third linear cam profile (502C) (not visible in FIG. 5 but shown in FIGS. 27 through 31), and a fourth linear cam profile (502D). The cam drum (204) further includes four helical cam profiles including a first helical cam profile (504A), a second helical cam profile (504B) (shown in FIG. 32), a third helical cam profile (504C) (shown in FIG. 30), and a fourth helical cam profile (504D). Each of the linear cam profiles (502A) through (502D) include a start point, an end point, a one-way ratchet extending between the start point and the end point, and a slot through which the EOL lock (208) is configured to protrude in and out of the cam drum (204) when pulling out the thumb pad (202) towards the proximal end. For example, FIG. 5 depicts the first linear cam profile (502A) having a start point (506A), an end point (508A), a one-way ratchet (510A) extending between the start point (506A) and the end point (508A), and a slot (511A). Though, it is not shown in FIG. 5, it is to be understood that, similarly, the second, third, and fourth linear cam profiles (502B) through (502D) have their own start point (506B) through (506D), end point (508B) through (508D), one-way ratchet (510B) through (510D), and slot (511B) through (511D), respectively.

In one exemplary embodiment, similar to the linear cam profiles (502A-D), each of the helical cam profiles (504A-D) has its own start point and end point. For example, FIG. 5 depicts a start point (512A) and an end point (514A) associated with the first helical cam profile (504A). Similarly, it is to be understood that the second, third, and fourth helical cam profiles (504B) through (504D) have their own start point (512B) through (512D), and end points (514B) through (514D), respectively. In certain embodiments, the first helical cam profile (504A) connects the first linear cam profile (502A) and the second linear cam profile (502B), as shown in FIG. 5. Similarly, the second helical cam profile (504B) connects the second linear cam profile (502B) and the third linear cam profile (502C). The third helical cam profile (504C) connects the third linear cam profile (502C) and the fourth linear cam profile (502D). The fourth helical cam profile (504D) connects the fourth linear cam profile (502D) and the first linear cam profile (502A). It may be noted that start points of the helical cam profiles (504A-D) immediately follow end points of the linear cam profiles (502A-D), respectively. Similarly, start points of the linear cam profiles (502A-D) immediately follow end points of the helical cam profiles (504A-D), respectively.

In addition, each of these linear cam profiles (502A-D) and helical cam profiles (504A-D) has a gradient path having a slope that gradually increases along its length from its start point to its end point. For example, the first linear cam profile (502A) has a gradient path having a slope that gradually increases along its length with a maximum slope towards its end point (508A). Similarly, the first helical cam profile (504A) has a gradient path having a maximum slope at its end point (514A). These gradient paths associated with the linear cam profiles (502A-D) and the helical cam profiles (504A-D) define paths to be followed by the levers (326) and (330) of the thumb pad (202) while setting and delivering a dose, as described in detail in with reference to FIGS. 6 through 8.

Figure 6:
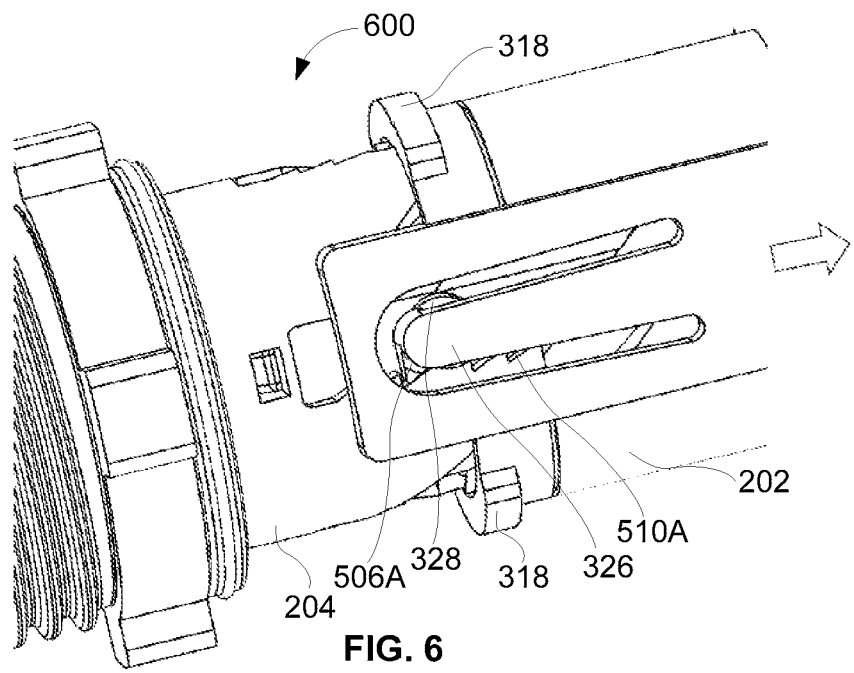
FIG. 6 is a schematic representation illustrating one example of a position of the thumb pad with respect to the cam drum of FIG. 2 when disposed in an initial state before pulling out the thumb pad for setting a dose.

FIG. 6 is a schematic representation (600) illustrating a position of the thumb pad (202) with respect to the cam drum (204) of FIG. 2 at an initial state before pulling out the thumb pad (202) for setting a dose, according to one embodiment of the present disclosure. In one exemplary embodiment, the lever (326) having the pawl (328) is placed in an engaged position with the start point (506A) of the ratchet (510A) at the initial state. Although not depicted in FIG. 6, it is to be understood that the lever (330) having the pawl (332) is similarly placed in an engaged position with the start point (506C) of the ratchet (510C). The user can set the dose by pulling out the thumb pad (202) in the direction of the proximal end (104). When the user pulls out the thumb pad (202), the pawls (328) and (332) ride on the ratchets (510A) and (510C), respectively to enable a movement of the thumb pad (202) in the direction of the proximal end (104). In addition, riding of the pawls (328) and (332) on the ratchets (510A) and (510C), respectively provides an audible feedback to the user. If the user does not fully pull out the thumb pad (202) while setting the dose, and attempts to inject a medication, the user is prevented from doing so, as described with reference to FIG. 7.

Figure 7:
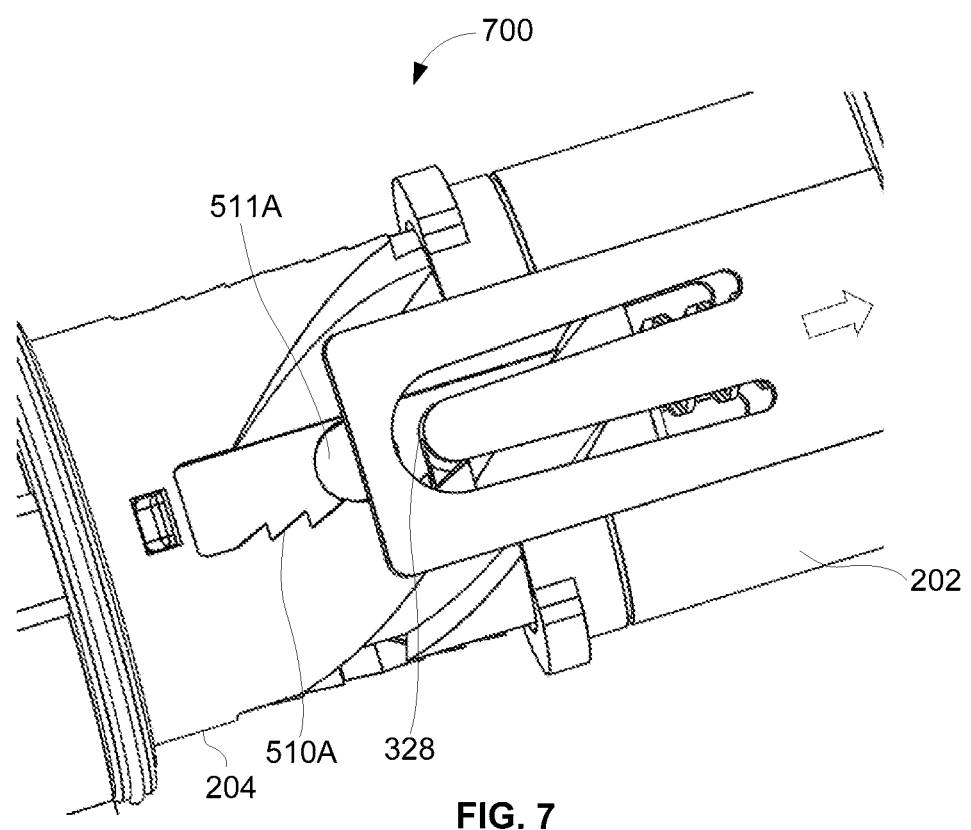
FIG. 7 is a schematic representation illustrating one example of a position of the thumb pad with respect to the cam drum of FIG. 2 when pulling out the thumb pad from the initial state for setting a dose.

FIG. 7 is a schematic representation (700) illustrating an exemplary position of the thumb pad (202) with respect to the cam drum (204) of FIG. 2 when pulling out the thumb pad (202) from the initial state for setting a dose, according to one embodiment of the present disclosure. As previously noted, when the user attempts to inject the medication without pulling the thumb pad (202) completely out, the thumb pad (202) does not move forward. Because, the pawls (328) and (332) that are currently positioned and engaged with the ratchets (510A) and (510C) are one-way ratchets. The one-way ratchets (510A) and (510C) allow the thumb pad (202) to move only along a reverse path in the direction of the proximal end (104). In other words, the one-way ratchets (510A) and (510C) do not allow the thumb pad (202) to move along a forward path in the direction of the distal end (106), and hence, the dose would not be delivered. Once the dose is set by completely pulling out the thumb pad (202), the dose is delivered as explained with reference to FIG. 8.

Figure 8:
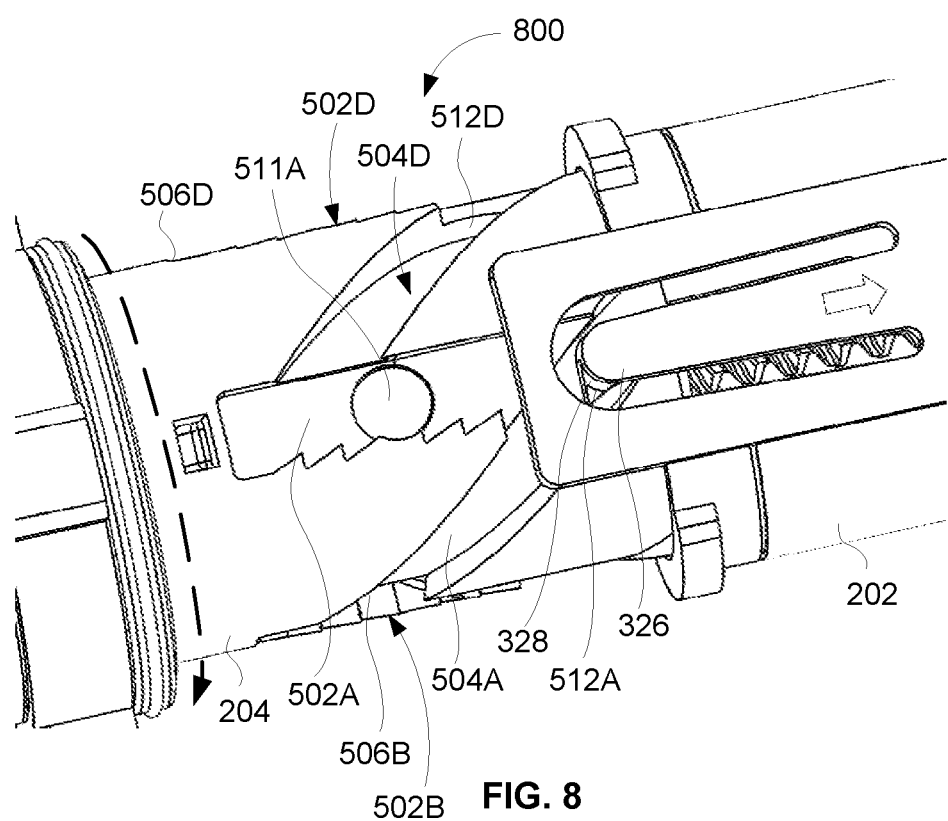
FIG. 8 is a schematic representation illustrating one example of a position of the thumb pad with respect to the cam drum of FIG. 2 at an end of a first dose setting stage.

FIG. 8 is a schematic representation (800) illustrating a position of the thumb pad (202) with respect to the cam drum (204) of FIG. 2 at an end of a first dose setting stage, according to one embodiment of the present disclosure. In certain embodiments, at the end of the first dose setting stage, the pawls (328) and (332) are configured to complete taking the gradient paths defined by the first and third linear cam profiles (502A) and (502C), respectively, and are placed in a ready position to take gradient paths defined by the helical cam profiles. It is to be noted that, in general, the lever (326) having the pawl (328) and the lever (330) having the pawl (332) are configured to take linear cam profiles for setting the dose, and to take helical cam profiles for delivering the dose.

More particularly, at the end of the first dose setting stage, the first lever (326) having the pawl (328) is configured to be placed at the start point (512A) of the first helical cam profile (504A). Similarly, it is be understood that, the second lever (330) having the pawl (332) is configured to be placed at the start point (512C) of the third helical cam profile (504C). At this stage, the thumb pad (202) is pushed forward towards the distal end (106) to deliver the dose, and thereby causing the first lever (326) having the pawl (328) rides on the first helical cam profile (504A) and the second lever (330) having the pawl (332) to ride on the third cam profile (504C). In one embodiment, the cam drum (204) is configured to rotate in a designated direction (e.g., a clockwise direction) whenever the pawls (328) and (332) ride over any helical cam profiles (504A-D). Further, when the pawls (328) and (332) complete taking the first and third helical paths (504A) and (504C) respectively, the cam drum (204) is configured to complete one rotation by a designated angle (e.g., 90°).

In one embodiment, one complete rotational movement of the cam drum (204) by the designated angle causes the lead screw (216) to rotate and move a designated linear distance to deliver a fixed dose. To that end, a keyway (902) (shown in FIG. 9) is provided at one end (e.g., a proximal end) of the cam drum (204). The keyway (902) is a slot made to engage the lead screw (216) with the cam drum (204). In one exemplary embodiment, the lead screw (216) is coupled to the keyway (902) using a tongue and groove joint. Since, the lead screw (216) is coupled to the cam drum (204) through the keyway (902), rotation of the cam drum (204) by the designated angle causes rotation of the lead screw (216) too, and therefore, the lead screw (216) moves forward by a designated distance in the direction of the distal end (106) to deliver the fixed dose.

In certain embodiments, at the end of the first dose delivery, the pawls (328) and (332) are configured to complete paths defined by the first and third helical cam profiles (504A) and (504C), respectively. Subsequently, the pawls (328) and (332) are configured to be placed in a ready position at start points (506B) and (506D) associated with the second and fourth linear cam profiles (502B) and (502D), respectively for a second cycle of dose setting.

Similarly, at an end of a second dose setting stage, the pawls (328) and (332) are configured to be placed at start points (512B) and (512D) of the second and fourth helical cam profiles (504B) and (504D), respectively. Upon pushing the thumb pad (202) for a second dose delivery, the pawls (328) and (332) take paths defined by the second and fourth helical cam profiles (504B) and (504D) to deliver the fixed dose for the second time. Thus, the pawls (328) and (332) are configured to ride on linear cam profiles on the cam drum (204) and to be placed at start points of helical cam profiles adjacent to the linear cam profiles at the end of every dose set stage. The pawls (328) and (332) are further configured to ride on helical cam profiles on the cam drum (204) and to be placed at start points of linear cam profiles adjacent to the helical cam profiles at the end of every dose delivery stage.

Figure 9:
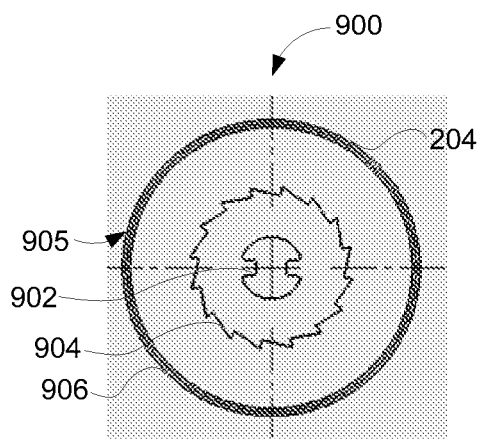
FIG. 9 illustrates a left side view of the cam drum depicted in FIG. 2.

FIG. 9 illustrates a left side view (900) of the cam drum (204) of FIG. 2, according to one embodiment of the present disclosure. The cam drum (204) is configured to rotate only in a desired direction while delivering the dose. In one embodiment, the desired direction is a clockwise direction. To that end, the cam drum (204) is provided with a one-way ratchet (904) that mates with a pawl (shown in FIG. 19) associated with the pawl nut (214). In one embodiment, teeth of the one-way ratchet (904) are designed in such a way that the one-way ratchet (904) and the pawl arrangement allow the cam drum (204) to rotate only in a clockwise direction. When the cam drum (204) attempts to rotate in an anti-clockwise direction for any reasons, the one-way ratchet (904) is locked with the pawl, and hence, the cam drum (204) is prevented from rotating in the anti-clockwise direction. Similarly, it is to be understood that, the cam drum (204) can also be made to rotate only in the anti-clockwise direction by designing the teeth of the one-way ratchet (904) in such a way that the one-way ratchet (904) and the pawl arrangement allow the cam drum (204) to rotate only in the anti-clockwise direction. The cam drum (204) further includes a barrel-engaging surface 905 and high points (906) that prevent friction, which occurs between the cam drum (204) and other components of the dispensing device (102) while the cam drum (204) is rotating.

Figure 10:
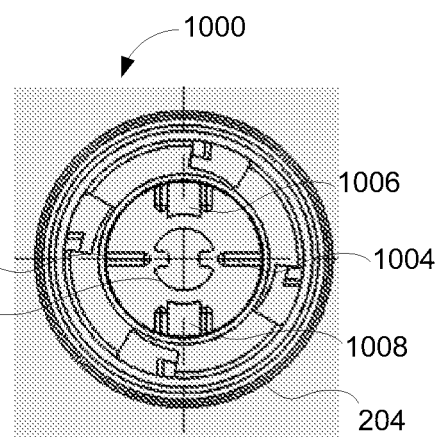
FIG. 10 illustrates a right side view of the cam drum depicted in FIG. 2.

Further, FIG. 10 illustrates a left side cross-sectional view (1000) of the cam drum (204) of FIG. 2, according to one embodiment of the present disclosure. In one exemplary embodiment, the cam drum (204) includes guide ribs (1002 and 1004) that are placed horizontally at opposite sides (e.g., left and right) of the keyway (902) and are configured to face each other. The guide ribs (1002 and 1004) guide the lead screw (216) to pass through the keyway (902) when the cam drum (204) is rotated by the actuation of the thumb pad (202) towards the distal end (106) during dose delivery. In certain embodiments, the cam drum (204) further includes rotation prevention ribs (1006 and 1008) that are placed vertically at opposite sides (e.g., top and bottom) of the keyway (902). The rotation prevention ribs 1006 and 1008 are configured to hold the EOL adapter (206) tightly between the rotation prevention ribs (1006 and 1008) and to prevent disengagement or rotation of the EOL adapter (206) from its locked position with the cam drum (204).

Figure 11:
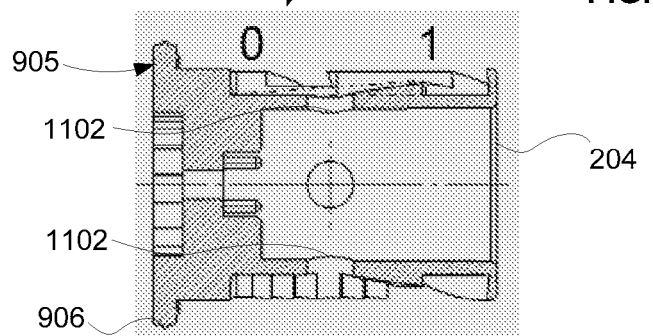
FIG. 11 illustrates a front cross-sectional view of the cam drum depicted in FIG. 2.

FIG. 11 illustrates a front cross-sectional view (1100) of the cam drum (204) of FIG. 2, according one embodiment of the present disclosure. In one embodiment, the cam drum (204) includes cut out portions (1102) for locking the EOL adapter (206) with the cam drum (204), as described with reference to FIG. 12. The EOL adapter (206), the EOL locks (208), and the EOL elastic members (210) are configured to prevent a user from setting a dose once a designated final dose is delivered and the cartridge (220) is empty, as described in detail with reference to FIGS. 12 through 16.

Figure 12:
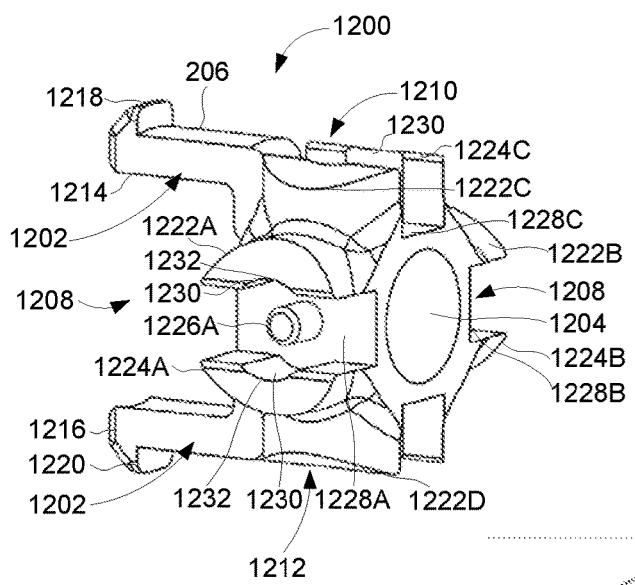
FIG. 12 illustrates a front perspective view of an EOL adapter depicted in FIG. 2.

FIG. 12 illustrates a front perspective view (1200) of the EOL adapter (206) of FIG. 2, according to one embodiment of the present disclosure. The EOL adapter (206) includes one or more legs (1202), a center hole (1204), a left portion (1206), a right portion (1208), a top portion (1210), and a bottom portion (1212). In one exemplary embodiment, the one or more legs (1202) correspond to a first leg (1214) and a second leg (1216) in the EOL adapter (206). The first leg (1214) includes a first snap feature (1218) and the second leg (1216) includes a second snap feature (1220). The EOL adapter (206) is locked with the cam drum (204) by locking the first snap feature (1218) and the second snap feature (1220) with the cut out portions (1102) (shown in FIG. 11) of the cam drum (204). The center hole (1204) allows the lead screw (216) to pass through the EOL adapter (206).

In certain embodiments, structures of the left portion (1206), the right portion (1208), the top portion (1210), and the bottom portion (1212) of the EOL adapter (206) are substantially the same. Hence, for the sake of simplicity, only components associated with the left portion (1206) of the EOL adapter (206) are explained in the subsequent paragraph. It is to be understood that, similarly, the components associated with the right, top, and bottom portions (1208, 1210, and 1212), respectively, have structural arrangements and functionalities that are similar to the corresponding components of the left portion (1206).

In one embodiment, the left portion (1206) of the EOL adapter (206) includes a first flexure (1222A), a second flexure (1224A), a rounded peg (1226A), and an EOL lock seating surface (1228A) formed between the first flexure (1222A) and the second flexure (1224A). Similarly, it is to be understood that each of the right, top, and bottom portions (1208, 1210, and 1212) of the EOL adapter (206) have its own first flexures (1222B) through (1222D), second flexures (1224B) through (1224D), rounded pegs (1226B) through (1226D), and EOL lock seating surface (1228B) through (1228D).

In one embodiment, the first and second flexures (1222A) and (1224A) of the left portion (1206) include curvatures that correspond to an internal diameter of the cam drum (204). In addition, the first and second flexures (1222A) and (1224A) include cuts (1230) that extend along center portions (1232) of the first and second flexures (1222A) and (1224A). The cuts (1230) act as a rotation prevention feature that prevents the EOL lock (208) from rotating and disengaging from the EOL adapter (206). The rounded peg (1226A) supports the EOL elastic members (210) (shown in FIG. 15) on which the EOL lock (208) (shown in FIGS. 13 and 14) is configured to be positioned. In one embodiment, the EOL elastic members (210) are compression springs. The EOL lock seating surface (1228A) acts as a receiving surface that receives and seats the EOL lock (208) when the lever (326) compresses the EOL lock (208) during a dose-setting event, as described in detail with reference to FIG. 16.

Figure 13:
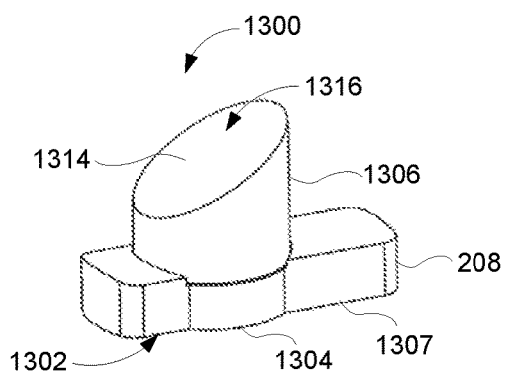
FIG. 13 illustrates a front perspective view of an EOL lock depicted in FIG. 2.
Figure 14:
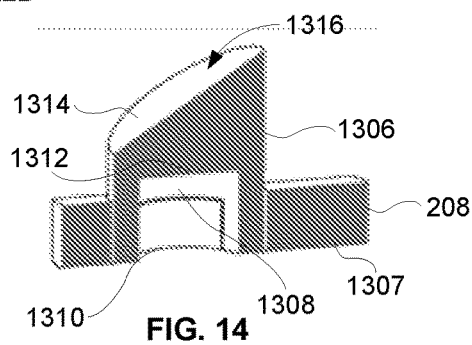
FIG. 14 illustrates a cross-sectional view of the EOL lock depicted in FIG. 13.

FIG. 13 illustrates a front perspective view (1300) of the EOL lock (208) of FIG. 2, according to one embodiment of the present disclosure. In certain embodiments, the dispensing device (102) includes four such EOL locks (208) that are substantially similar in structure and functionality. Hence, for the sake of simplicity, only a single EOL lock (208) is depicted and is described with reference to FIG. 13. The EOL lock (208) includes a base structure (1302) having a center portion (1304), an elevated portion (1306) that extends upwards from the center portion (1304) of the base structure (1302), and a flange-engaging portion (1307). The center portion (1304) includes an inner slot (1308) that extends from its bottom surface (1310) to a spring seating surface (1312) of the EOL lock (208) as shown in FIG. 14. The elevated portion (1306) includes an angular cutout (1314) disposed on a top surface (1316) of the elevated portion 1306. In one exemplary embodiment, the angular cutout (1314) disposed on the top surface (1316) of the elevated portion (1306) is wedge shaped and is a 30° angular cutout.

Figure 15:
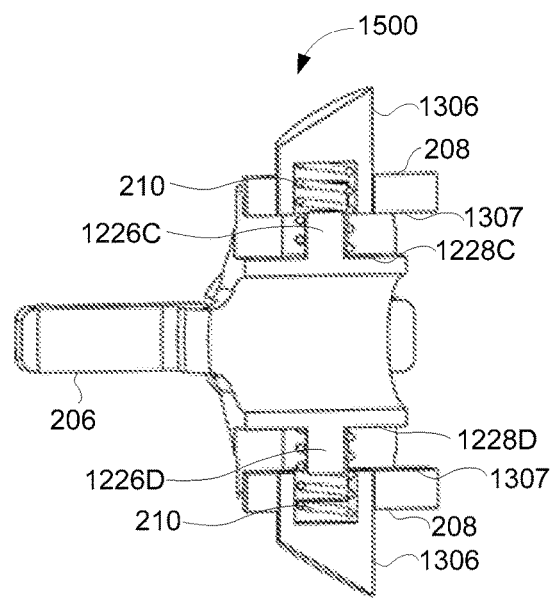
FIG. 15 illustrates a schematic representation of a portion of the EOL adapter having the EOL locks in an uncompressed state, according to one embodiment of the present disclosure.

In one embodiment, before coupling the EOL adapter (206) with the cam drum (204) by locking the first and second snap features (1218 and 1220) with the cut out portions (1102), each of the four EOL locks (208) is assembled with the EOL adapter (206). To that end, an EOL compression spring (210) (shown in in FIG. 15) is first mounted on each of the rounded pegs (1226A-D) (described in FIG. 12) of the EOL adapter (206), and subsequently, an EOL lock (208) is placed on the corresponding compression spring (210) (as shown in FIG. 15). In certain embodiments, the compression springs (210) undergo compression when the levers (328) and (332) ride on the elevated portions (1306) of the EOL locks (208) and make the elevated portions (1306) to protrude into the cam drum (204) to provide paths for the levers (328) and (332) to move further in the proximal direction (106). In addition, the compression springs (210) release stored energy after the levers (328) and (332) pass beyond the slots (511A-D) and make the elevated portions (1306) to protrude out of the cam drum (204).

Once the four EOL locks (208) are assembled with the EOL adapter (206), the EOL adapter (206) is coupled with the cam drum (204) using the snap features (1218 and 1220), such that, the elevated portion (1306) associated with each of the four EOL locks (208) protrudes out through the slots (511A-D) associated with the linear cam profiles (502A-D). Hence, in every dose setting process, when the thumb pad (202) is pulled out in the direction of the proximal end (104), each of the pawls (328) and (332) is configured to ride over a linear cam profile and to compress the elevated portion (1306) protruding out in the path of the linear cam profile.

For example, in the first dose setting stage, the pawls (328) and (332) ride on the first and third linear cam profiles (502A) and (502C), respectively, and compress the elevated portions (1306) of the EOL locks (208) that protrude out through the slots (511A) and (511C). The angular cutout (1314) of the elevated portion (1306) ensures smooth riding of the pawls (328) and (332) over the EOL locks (208) during a dose setting stage.

Figure 16:
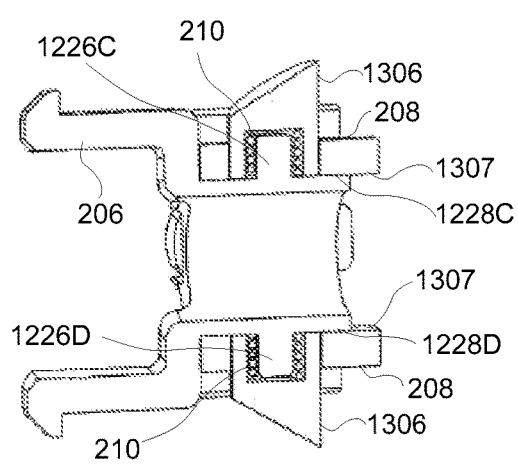
FIG. 16 illustrates a schematic representation of a portion of the EOL adapter having the EOL locks in a compressed state, according to one embodiment of the present disclosure.

FIG. 15 illustrates a schematic representation (1500) of a portion of the EOL adapter (206) having the EOL locks (208) in an uncompressed state, according to one embodiment of the present disclosure. More particularly, FIG. 15 depicts the EOL adapter (206) having the EOL compression springs (210) that are mounted on the rounded pegs (1226C) and (1226D) of the EOL adapter (206). In addition, the EOL locks (208) are placed on the EOL compression springs (210). As previously noted, during dose setting stages, the pawls (328) and (332) are configured to ride over the elevated portions (1306) of the EOL locks (208), thus causing compression of the EOL compression springs (210) (shown in FIG. 16) and protrusion of the elevated portions (1306) into the cam drum (204) to ensure a smooth ride of the pawls. In addition, when the elevated portions (1306) protrude into the cam drum (204), the EOL locks (208) are compressed and are seated on the EOL lock seating surfaces (1228C) and (1228D), as shown in FIG. 16. After the pawls (328) and (332) compress the EOL locks (208) and pass beyond slots on the linear cam profiles (402), the energy stored by the EOL compression springs (210) is released, thus causing the EOL locks (208) to protrude out of the slots again.

In certain embodiments, once a final dose is delivered and the cartridge (220) is empty, a flange (shown in FIG. 20) of the lead screw (216) is configured to be placed under the EOL locks (208). More particularly, the flange is configured to be placed under the flange-engaging portion (1307) of the EOL locks (208). When a user attempts to set a dose when the cartridge (220) is empty by pulling out the thumb pad (202), the pawls (328) and (332) ride on linear cam profiles until the pawls (328) and (332) reach the elevated portions (1306) of the EOL lock 208. The elevated portions (1306) stop the pawls (328) and (332) from riding further beyond the elevated portions (1306) as the EOL locks (208) that are supposed to be compressed when the pawls (328) and (332) ride on the EOL locks (208) are prevented from undergoing compression due to presence of the flange (2002) under the EOL locks (208). Therefore, the EOL locks (208) act as a barrier for movement of the pawls (328) and (332) and prevent the thumb pad (202) from moving further and from setting the dose.

Figure 17:
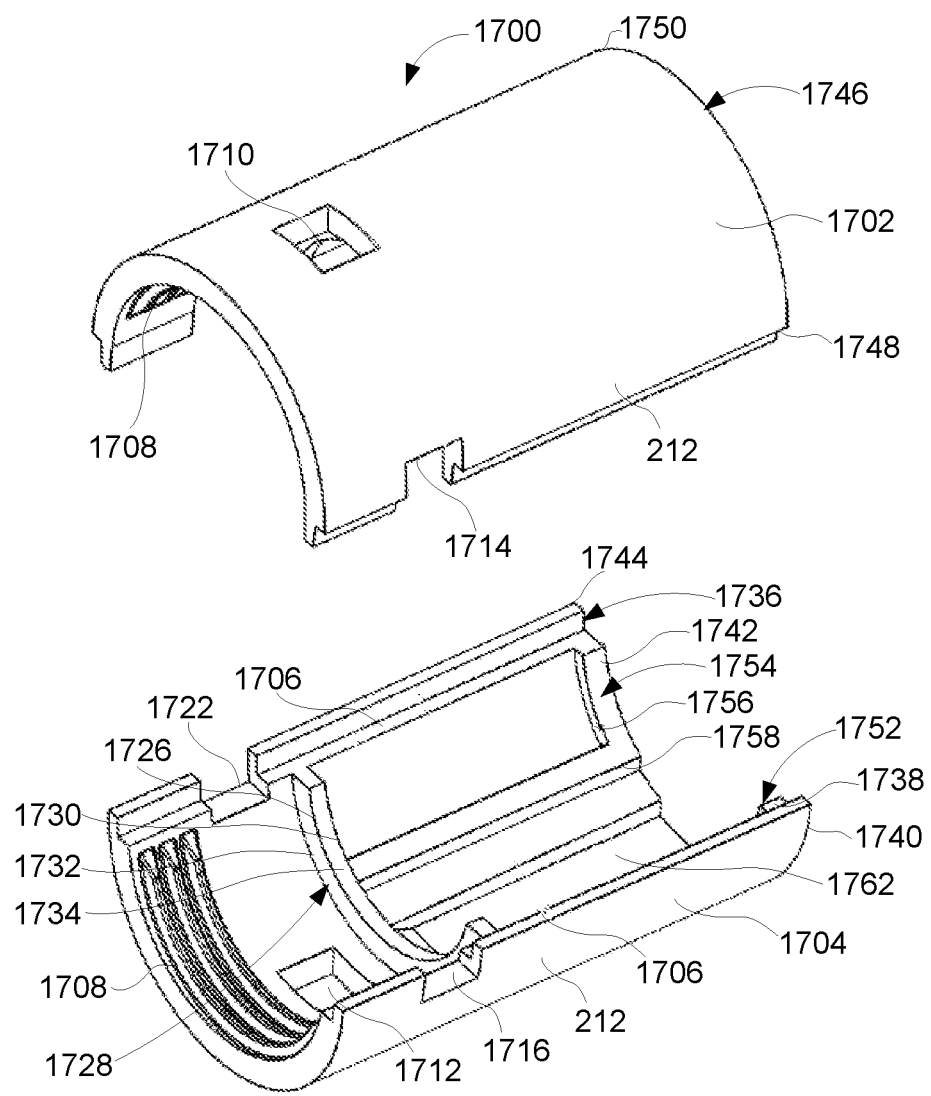
FIG. 17 illustrates an exploded view of a pen barrel depicted in FIG. 2.

FIG. 17 illustrates an exploded view (1700) of the pen barrel (212) of FIG. 2, according to one of the present disclosure. In certain embodiments, the pen barrel (212) corresponds to a structure including an upper half (1702) and a lower half (1704). Particularly, the pen barrel (212) acts as a casing that encloses and protects components of the dispensing device (102). Both upper half (1702) and the lower half (1704) of the pen barrel (212) include lip lock features (1706) that secure both halves of the pen barrel (212) together. In an alternative embodiment, the upper half (1702) and the lower half (1704) of the pen barrel (212) are welded together by ultrasonic means or by solvent bonding techniques such that the pen barrel (212) is made as a single rigid body and a non-resettable assembly. The upper half (1702) and the lower half (1704) of the pen barrel (212) further include thread features (1708) for securing the cartridge holder (222) with the pen barrel (212).

In one embodiment, the upper half (1702) of the pen barrel (212) includes a slot (1710) disposed on its surface. Similarly, the lower half (1704) of the pen barrel (212) includes a slot (1712) disposed on its surface. In addition, upon securing both halves of the pen barrel (212) together, a partial slot (1714) of the upper half (1702) matches with a partial slot (1716) of the lower half (1704), thereby forming a complete slot (1718). Similarly, a partial slot (1720) (not visible in FIG. 17) of the upper half (1702) matches with a partial slot (1722) of the lower half (1704), thereby forming a complete slot (1724). The slots (1710, 1712, 1718, and 1724), thus formed, are configured to accommodate rib portions (shown in FIG. 18) of the pawl nut (214) and prevent the pawl nut (214) from rotating during dose setting and dose delivery stages.

In certain embodiments, each half of the pen barrel (212) includes a semi-circular rib (1726). FIG. 17 depicts only the semi-circular rib (1726) associated with the lower half (1704) of the pen barrel (212). However upon securing both the halves (1702) and (1704) together, a complete circular rib (1728) is formed. The circular rib (1728) includes a front wall surface (1730), a rear wall surface (1732), and a slot (1734) disposed between the front wall surface (1730) and the rear wall surface (1732). In one embodiment, the circular rib (1728) includes the slot (1734) into which the barrel-engaging surface 905 of the cam drum (204) is positioned and is secured. Thus, the circular rib (1728) acts a lock feature for the cam drum (204) and prevents the cam drum (204) from moving linearly forward or rearward, using the wall surfaces (1730 and 1732), while setting and delivering the dose.

In addition, the pen barrel (212) includes a first arc shaped rib (1738) positioned at a right corner (1740) and a second arc shaped rib (1742) positioned at a left corner of a front surface (1736) corresponding to the lower half (1704) of the pen barrel (212). Though it is not shown in FIG. 17, it is to be understood that, similarly, the pen barrel (212) also includes a first arc shaped rib positioned at a right corner (1748) and a second arc shaped rib positioned at a left corner (1750) of a front-end surface corresponding to the upper half (1702) of the pen barrel (212). Upon securing both the halves together, the first arc shaped ribs associated with the upper half (1702) and the lower half (1704) form a semi-circular rib (1752), and the second arc shaped ribs of the halves form another semi-circular rib (1754). However, FIG. 17 depicts only a portion of the semi-circular ribs (1752 and 1754). As previously noted, while operating the dispensing device (102) for setting the dose, the thumb pad (202) is pulled completely out, causing the snap locks (318) of the thumb pad (202) to engage against inner walls (1756) of the semi-circular ribs (1752 and 1754), and thus preventing the thumb pad (202) from moving further.

In certain embodiments, the lower half (1704) of the pen barrel (212) includes a first guiding surface (1758) and a second guiding surface (1760) (not shown in FIG. 17) that is disposed at a designated distance to the right of the first guiding surface (1758). A distance between the first guiding surface (1758) and the second guiding surface (1760) is selected such that one of the extensions (316) of the thumb pad (202) fits within and engages against the guiding surfaces (1758 and 1760). While setting and delivering the dose, the guiding surfaces (1758) and (1760) guide the thumb pad (202) to move linearly and prevent a circular rotation of the thumb pad (202). If any attempts are made to rotate the thumb pad (202), the thumb pad (202) is prevented from rotating due to an engagement between the extension (316) and the guiding surfaces (1758 and 1760). Similarly, it is to be understood that, the upper half (1702) of the pen barrel (212) also includes guiding surfaces such that another extension (316) of the thumb pad (202) fits, engages, and slides against the corresponding guiding surfaces.

In addition, when the components of the dispensing device (102) are assembled together, the pen barrel (212) is configured to partially enclose the thumb pad (202), while completely enclosing the cam drum (204) and other components of the dispensing device (102). It is to be noted that there is adequate space between the thumb pad (202) and an inner surface of the pen barrel (212) to prevent interference of the pen barrel (212) with the levers (326) and (330) of the thumb pad (202) during dose setting and dose delivery. Provision of adequate space also ensures smooth riding of the levers (326) and (330) on the linear cam profiles (402) and the helical cam profiles (404) without being impeded by the pen barrel (212). To that end, a depression (1762) is provided in the lower half (1704) of the pen barrel (212). Similarly, it may be noted that the upper half (1702) of the pen barrel (212) also includes a depression. The depressions provided at both halves of the pen barrel (212) provide the adequate gap between the thumb pad (202) and the pen barrel (212) and enable smooth riding of the levers (326) and (330) while setting and delivering the dose.

In certain embodiments, while delivering the dose, the cam drum (204) is configured to rotate only in a desired direction (e.g., a clockwise direction) and is prevented from rotating in an opposite direction (e.g., an anti-clockwise direction). To that end, the pawl nut (214) is provided. An exemplary structure and functioning of the pawl nut (214) is described in detail with reference to FIG. 18.

Figure 18:
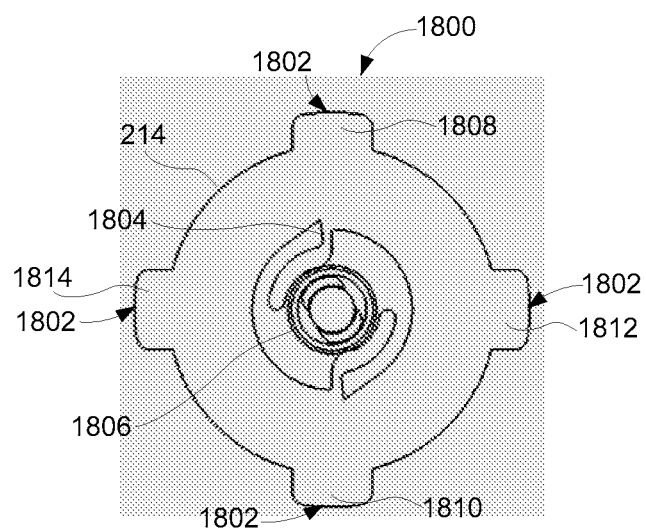
FIG. 18 is a front perspective view of a pawl nut depicted in FIG. 2.

FIG. 18 is a front perspective view (1800) of an exemplary embodiment of the pawl nut (214). The pawl nut (214) includes a plurality of ribs (1802), a one-way pawl (1804), and a slot having internal threads (1806) through which the lead screw (216) advances towards the distal end (106) while delivering the dose. In one exemplary embodiment, the plurality of ribs (1802) includes a first rib (1808), a second rib (1810), a third rib (1812), and a fourth rib (1814). Each of these ribs is configured to be secured to slots of the pen barrel (212) and be placed in a locked condition with respect to the pen barrel (212) to prevent rotation of the pawl nut (214) during dose delivery. More particularly, the ribs (1808), (1810), (1812), and (1814) are secured to the slots (1710, 1712, 1718, and 1724), respectively. The functionalities of the one-way pawl (1804) are better understood with respect to FIG. 19.

Figure 19:
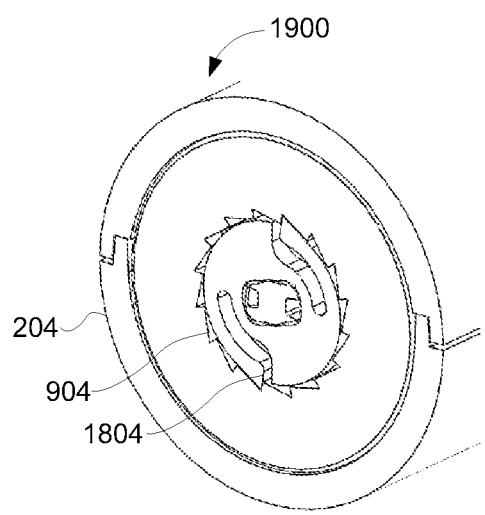
FIG. 19 is a schematic representation illustrating one-example embodiment of a one-way pawl of the pawl nut that is placed in an engaged position with a one-way ratchet of the cam drum depicted in FIG. 2.

FIG. 19 is a schematic representation (1900) that illustrates the one-way pawl (1804) that is placed in an engaged position with respect to the one-way ratchet (904) of the cam drum (204), according to one embodiment of the present disclosure. As previously noted, teeth of the one-way ratchet (904) are designed in such a way that the one-way ratchet (904) and the one-way pawl (1804) arrangement allow the cam drum (204) to rotate, for example, only in a clockwise direction. If any attempts are made to rotate the cam drum (204) in an anti-clockwise direction, the one-way ratchet (904) becomes locked with the one-way pawl (1804), thus preventing the cam drum (204) from rotating in the anti-clockwise direction. In addition, when the cam drum (204) is rotated in the clockwise direction during dose delivery, the one-way pawl (1804) slides up and over the teeth of the one-way ratchet (904) and provides audible feedback to a user. The one-way ratchet (904) and the one-way pawl (1804) arrangement also ensures the lead screw (216) cannot be rotated in an undesired direction (e.g., the anti-clockwise direction) because of the lead screw (216) being positively locked with the cam drum (204) that is configured to rotate only in the desired direction.

Referring back to FIG. 18, the internal threads (1806) of the pawl nut (214) have a pitch that corresponds to a pitch of the lead screw (216). In one embodiment, the internal threads (1806) associated with the pawl nut (214) are right-handed screw threads. Since the pitches of the internal threads (1806) and the lead screw (216) correspond to each other, the lead screw (216) advances and moves towards the distal end (106) by a designated distance when the cam drum (204) completes its one rotation (e.g., by 90°) during dose delivery. Forward movement of the lead screw (216) pushes a stopper in the cartridge (220) to deliver the fixed dose.

Figure 20:
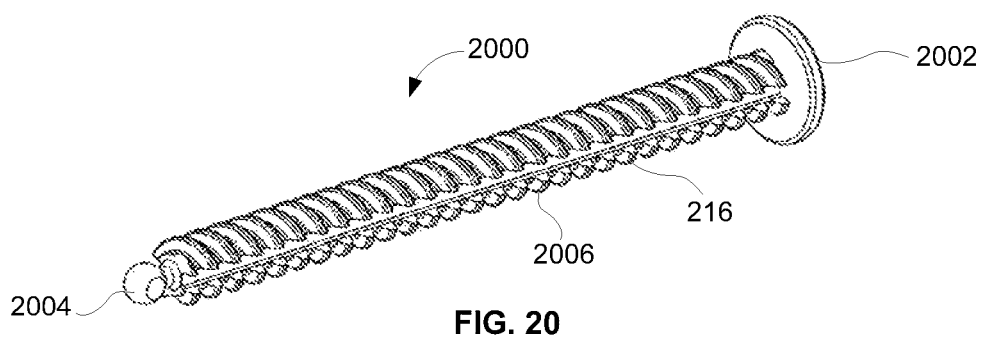
FIG. 20 illustrates a top perspective view of a lead screw depicted in FIG. 2.

FIG. 20 illustrates a top perspective view (2000) of the lead screw (216) of FIG. 2, according to one embodiment of the present disclosure. The lead screw (216) includes a flange (2002), a universal ball joint (2004), and internal threads (2006) that extend between the flange (2002) and the universal ball joint 2004. As previously noted, with reference to description of FIGS. 15 and 16, once a final dose is delivered and the cartridge (220) is empty, the flange (2002) is configured to be placed under the EOL locks (208). The flange (2002) prevents movements of the EOL locks (208) against the EOL compression springs (210) mounted on the EOL adapter (206), and thereby enables the EOL locks (208) to stop movements of the levers (326) and (330) through the linear cam profiles (402). Thus, the flange (2002) ensures that the user would never able to set the dose after the end of life (EOL) of the dispensing device (102).

In one embodiment, the internal threads (1806) associated with the lead screw (216) are right-handed screw threads. A distance by which the lead screw (216) is supposed to move, due to one complete rotation (e.g., by 90°) of the cam drum (204), is adjusted based on a pitch associated with the lead screw (216). In one embodiment, the dispensing device (102) is configured to be used multiple times until the cartridge (220) becomes empty, and each time, the dispensing device (102) is configured to deliver the fixed dose. In this embodiment, the pitch of the lead screw (216) is selected such that the lead screw (216) advances and moves forward by a designated distance each time when the dose is delivered. Since, the lead screw (216) moves by the same linear distance each time, the lead screw (216) also pushes and moves a stopper within the cartridge (220) gradually by the same distance, to deliver the fixed dose multiple times.

In an alternative embodiment, the dispensing device (102) is configured to be used only one time. All the medicaments accommodated with the cartridge (220) are configured to be delivered by a single actuation of the thumb pad (202) towards the distal end (106) of the dispensing device (102). In this embodiment, the length or pitch of the lead screw (216) is selected such that one complete rotation of the cam drum (e.g., by 90°) causes the lead screw (216) to move by a designated distance and to push the stopper to an end of the cartridge (220). Thus, the dispensing device (102) can be configured to dispense all the medicaments by the single actuation of the thumb pad (202) by selecting a desired pitch of the lead screw (216). In certain embodiments, the lead screw (216) includes the universal ball joint (2004) that is adapted to be coupled to the push pad (218), as shown and described in detail with reference to FIG. 21.

Figure 21:
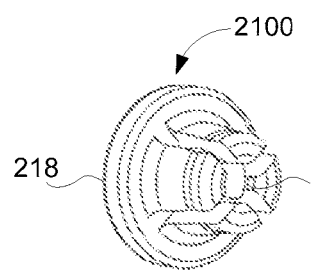
FIG. 21 illustrates a rear perspective view of a push pad depicted in FIG. 2.

FIG. 21 illustrates a rear perspective view (2100) of the push pad (218) of FIG. 2, according to one embodiment of the present disclosure. The universal ball joint (2004) of the lead screw (216) snap fits into a slot (2102) in the push pad (218). The push pad (218), thus snap fitted with the lead screw (216), allows the lead screw (216) to rotate within the push pad (218) and advance forward along with the lead screw (216) to deliver the medicaments carried by the cartridge (220). In addition, the push pad (218) is configured in a way such that the push pad (218) is prevented from rotating when the lead screw (216) rotates within the push pad (218) in order to reduce a frictional load on the cam drum (204).

Figure 22:
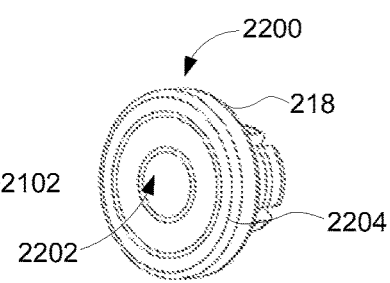
FIG. 22 illustrates a front perspective view of the push pad depicted in FIG. 2.

FIG. 22 illustrates a front perspective view (2200) of the push pad (218) of FIG. 2, according to one embodiment of the present disclosure. In one embodiment, when the lead screw (216) advances forward to deliver the dose, a front surface (2202) of the push pad (218) is configured to secure and to push the stopper (2302) (shown in FIG. 23) of the cartridge (220) to dispense the dose. The front surface (2202) of the push pad (218) includes high points (2204) that reduce a friction between the push pad (218) and the stopper (2302) of the cartridge (220).

Figure 23:
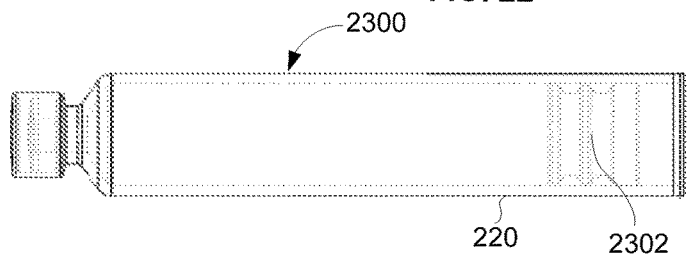
FIG. 23 illustrates a top view of a cartridge depicted in FIG. 2.
Figure 24:
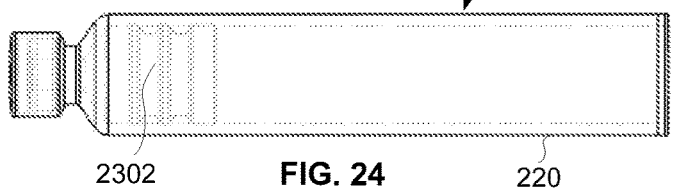
FIG. 24 is a top view illustrating one-example embodiment of the cartridge of FIG. 23 when it is empty after a final dose is delivered.

FIG. 23 illustrates a top view (2300) of the cartridge (220) of FIG. 2 that is filled with medicaments, according to one embodiment of the present disclosure. The cartridge (220) includes a stopper (2302) that is pushed by the push pad (218) due to advancement of the lead screw (216) towards the distal end (106) during dose delivery. Further, FIG. 24 illustrates a top view (2400) of the cartridge (220) of FIG. 2 when it is empty after a final dose is delivered, according to one embodiment of the present disclosure. In one embodiment, the cartridge (220) is housed within the cartridge holder (222) as described in detail with respect to FIG. 25.

Figure 25:
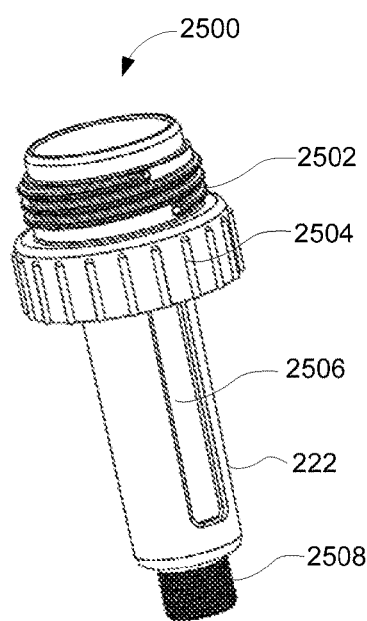
FIG. 25 illustrates a front perspective view of a cartridge holder depicted in FIG. 2.

FIG. 25 illustrates a front perspective view (2500) of the cartridge holder (222) of FIG. 2, according to one embodiment of the present disclosure. The cartridge holder (222) includes proximal external thread features (2502), a plurality of grip features (2504), a cutout window (2506), and distal external thread features (2508). In one embodiment, the proximal external thread features (2502) enable the cartridge holder (222) along with the cartridge (220) to secure into the pen barrel (212). The plurality of grip features (2504) enables the cartridge holder (222) to tighten and to fix securely to the pen barrel (212). Further, the cutout window (2506) allows the user to see the medicament level within the cartridge (220). The distal external thread features (2508) are provided for securing a needle to the cartridge holder (222). FIGS. 26A through 26I depict various stages of an exemplary assembly procedure for assembling various components (shown in the exploded view (200) of FIG. 2) of the dispensing device (102) to construct the dispensing device (102).

Figure 26A:
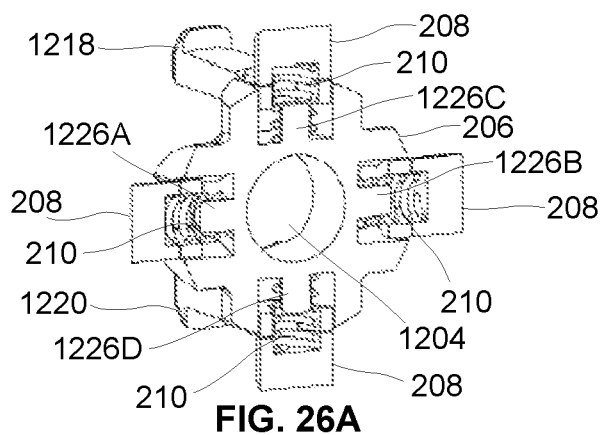
FIG. 26A is a schematic representation illustrating the EOL adapter assembled with EOL compression springs and the EOL locks of FIG. 2.

As shown in FIG. 26A, the EOL compression springs (210) and the EOL locks (208) are assembled with the EOL adapter (206), as described previously with reference to FIGS. 15 and 16. On each of the rounded pegs (1226A-D) associated with the EOL adapter (206), an EOL compression spring (210) is mounted, and subsequently, an EOL lock (208) is seated over each EOL compression spring (210). Subsequently, the EOL adapter (206), with the EOL locks (208) and the EOL compression springs (210), is snap fitted with the cam drum (204) by locking the first and second snap features (1218 and 1220) of the EOL adapter (206) with the cut out portions (1102) of the cam drum (204), as depicted in FIG. 26B.

In addition, while snap fitting the EOL adapter (206) with the cam drum (204), all four EOL locks (208) are pressed down against the EOL compression springs (210) to seamlessly place the EOL adapter (206) within the cam drum (204). Subsequent to snap fitting of the EOL adapter (206) with the cam drum (204) and upon releasing a force exerted by pressing down the EOL compression springs (210), the EOL compression springs (210) release stored energy and expand. In certain embodiments, the EOL adapter (206) is positioned within the cam drum (204) such that when the EOL compression springs (210) expand, the EOL locks (208) protrude out through the slots (511A-D) associated with the corresponding linear cam profiles (502A-D). More particularly, the elevated portion (1306) of an EOL lock (208) protrudes out through each of the slots (511A-D). FIG. 26B depicts one such exemplary embodiment in which the elevated portions (1306) associated with the two EOL locks (208) protrude out through the slots (511A) and (511C) associated with the linear cam profiles (502A) and (502C), respectively.

Figure 26B:
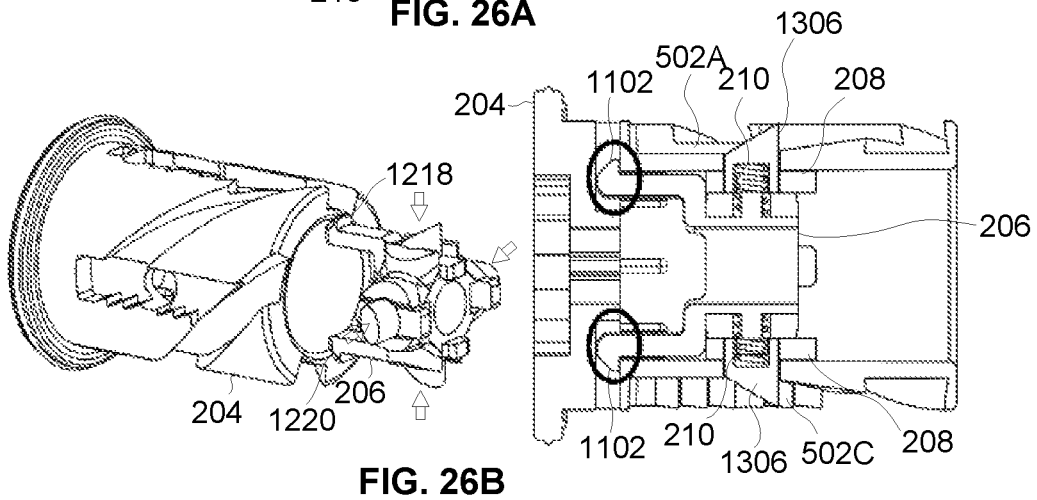
FIG. 26B is a schematic representation illustrating the EOL adapter of FIG. 26A secured within the cam drum of FIG. 2.

Similarly, though not shown in FIG. 26B, it is to be understood that, the other two EOL locks (208) protrude out through the slots (511B) and (511D) associated with the linear cam profiles (502B) and (502D), respectively. As previously noted, when the thumb pad (202) is pulled out for setting the dose, the levers (326) and (330) of the thumb pad (202) ride over the elevated portions (1306) of any two EOL locks (208), thereby causing the EOL compression springs 210, on which the EOL locks (208) are seated, to undergo compression (as shown in FIG. 16). Compression of the EOL compression springs (210) causes the elevated portions (1306) of the EOL locks (208) to protrude into the cam drum (204) to enable the levers (326) and (330) to move further towards the proximal end (104).

Figure 26C:
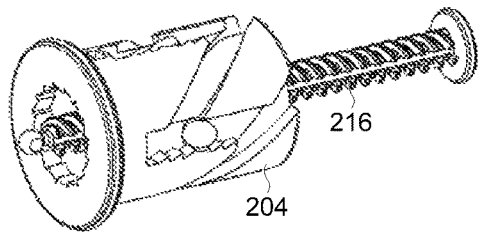
FIG. 26C is a schematic representation illustrating the lead screw inserted through the cam drum of FIG. 26B.
Figure 26E:
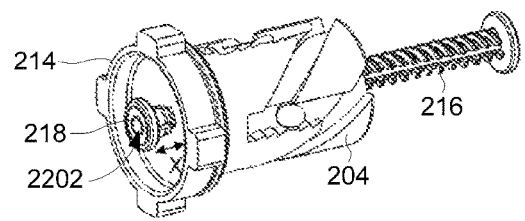
FIG. 26E is a schematic representation illustrating the push pad coupled with the lead screw of FIG. 26D.
Figure 26D:
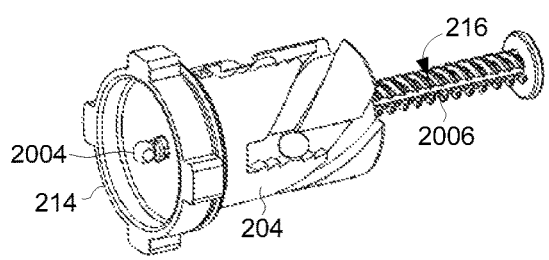
FIG. 26D is a schematic representation illustrating the pawl nut secured with the lead screw of FIG. 26C.

Following to snap fitting of the EOL adapter (206) with the cam drum (204), as shown in FIG. 26C, the lead screw (216) is positioned within the cam drum (204). While the lead screw (216) moves forward within the cam drum (204), the lead screw (216) is configured to pass through the center hole 1204 of the EOL adapter (206) and the keyway (902) of the cam drum (204). Subsequently, as shown in FIG. 26D, the pawl nut (214) is secured to the lead screw (216) by threading the internal threads (1806) of the pawl nut (214) against the internal threads (2006) of the lead screw (216). Further, as depicted in FIG. 26E, the push pad (218) is coupled with the lead screw (216) by snap fitting the universal ball joint (2004) of the lead screw (216) with the slot (2102) of the push pad (218). In one embodiment, a length of the push pad (218) is selected such that the front surface (2202) of the push pad (218) is placed at a designated distance from the pawl nut (214).

Figure 26F:
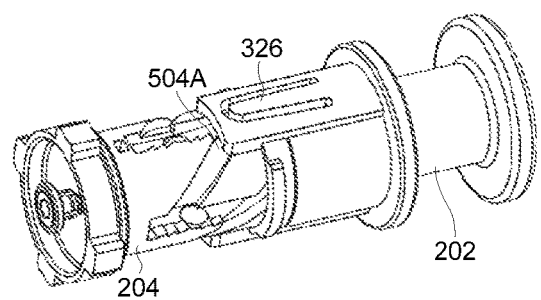
FIG. 26F is a schematic representation illustrating the thumb pad placed on helical cam profiles of the cam drum depicted in FIG. 26E.
Figure 26G:
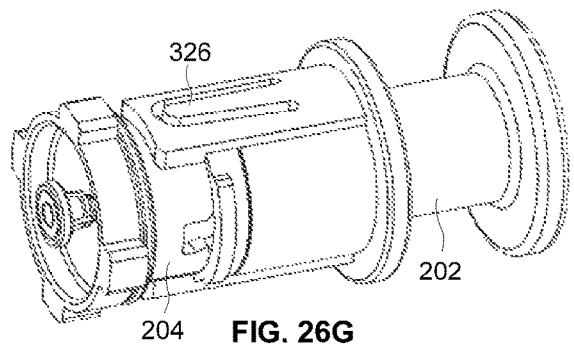
FIG. 26G is a schematic representation illustrating the thumb pad that is placed at start points of linear cam profiles of the cam drum depicted in FIG. 26E.

Once the push pad (218) is coupled with the lead screw (216), as depicted in FIG. 26F, the thumb pad (202) is placed on any two helical cam profiles selected from the helical cam profiles (504A-D). For example, the thumb pad (202) is placed on the helical cam profiles (504D) and (504B) when coupling the thumb pad (202) with the cam drum (204). Subsequently, the thumb pad (202) is pushed all the way through the helical cam profiles (504D) and (504B) such that the thumb pad (202) rides and completes the gradient paths defined by the helical cam profiles (504D) and (504B). The end points of the helical cam profiles (504D) and (504B) are immediately followed by the start points of the linear cam profiles (506A) and (506C). The levers (326) and (330) of the thumb pad (202) are configured to be positioned at the start points of the linear cam profiles (502A) and (502C) (as shown in FIG. 26G) after completing the gradient paths defined by the helical cam profiles (504D) and (504B). The levers (326) and (330), placed at the start points (506A) and (506C) of the linear cam profiles (502A) and (502C), are kept in a ready position to enable a user to set the dose.

Figure 26H:
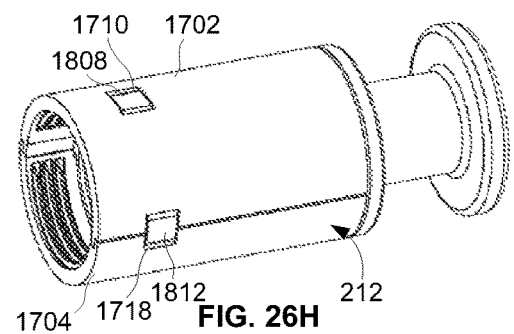
FIG. 26H is a schematic representation illustrating the pen barrel assembled with the pawl nut depicted in FIG. 26G.
Figure 26I:
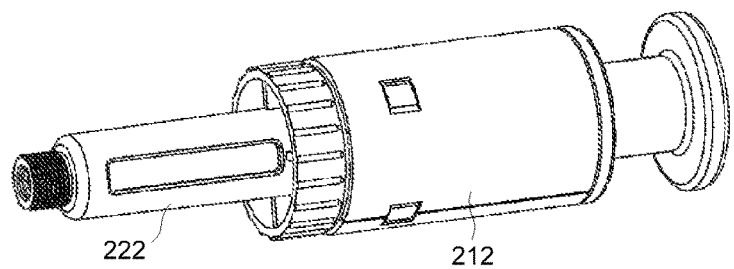
FIG. 26I is a schematic representation illustrating the cartridge holder coupled with the pen barrel of FIG. 26H.

FIG. 26H depicts an exemplary assembly of upper half (1702) and the lower half (1704) of the pen barrel (212) with the pawl nut (214) after the levers (326) and (330) are placed at the start points of the linear cam profiles, as described previously with reference to FIG. 17. More particularly, the pen barrel (212) is secured with the pawl nut (214) such that the ribs (1808), (1810), (1812), and (1814) are locked with the slots (1710, 1712, 1718, and 1724), respectively. FIG. 26H depicts the ribs (1808) and (1812) that are placed in a locked condition with respect to the slots (1710) and 1718, respectively. However, it is to be understood that the ribs (1810) and (1814) are similarly placed in a locked condition with respect to the slots (1712 and 1724), respectively. Subsequently, as shown in the FIG. 26I, the cartridge holder (222) along with the cartridge (220) is thread fitted into the pen barrel (212), thus resulting in completing the structural assembly of the dispensing device (102).

Figure 27:
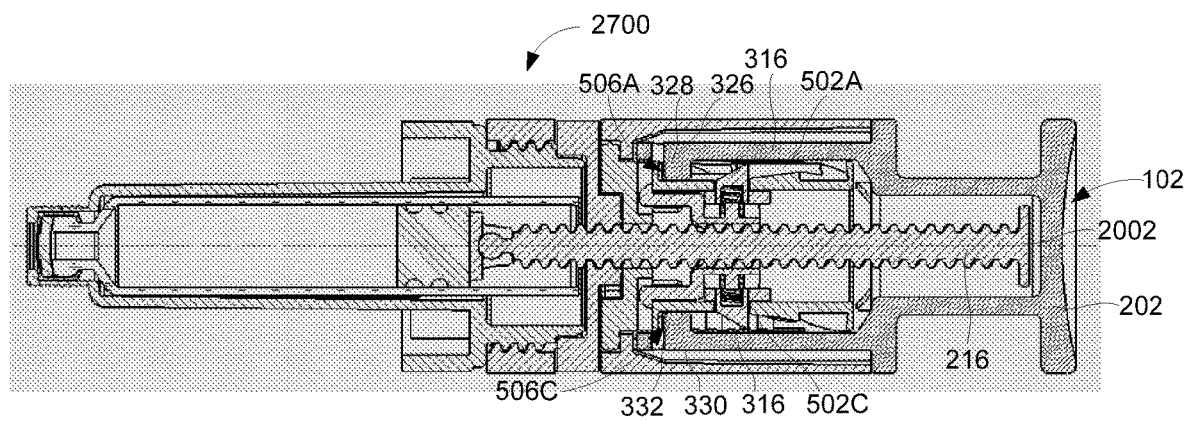
FIG. 27 illustrates a cross sectional view depicting an exemplary dispensing device of FIG. 1 at an initial state before setting a first dose.

Further, FIG. 27 illustrates a cross sectional view (2700) of the dispensing device (102) of FIG. 1 depicting an initial state of the dispensing device (102) before setting a first dose, according to one embodiment of the present disclosure. As previously noted, at the initial state, the lever (326) having the pawl (328) is disposed at the start point (506A) of the first linear cam profile (502A). The lever (330) having the pawl (332) is disposed at the start point (506C) of the third linear cam profile (502C). In one embodiment, the flange (2002) of the lead screw (216) engages against the thumb pad (202), and there is no gap disposed between the lead screw (216) and the thumb pad (202) at the initial state.

Figure 28:
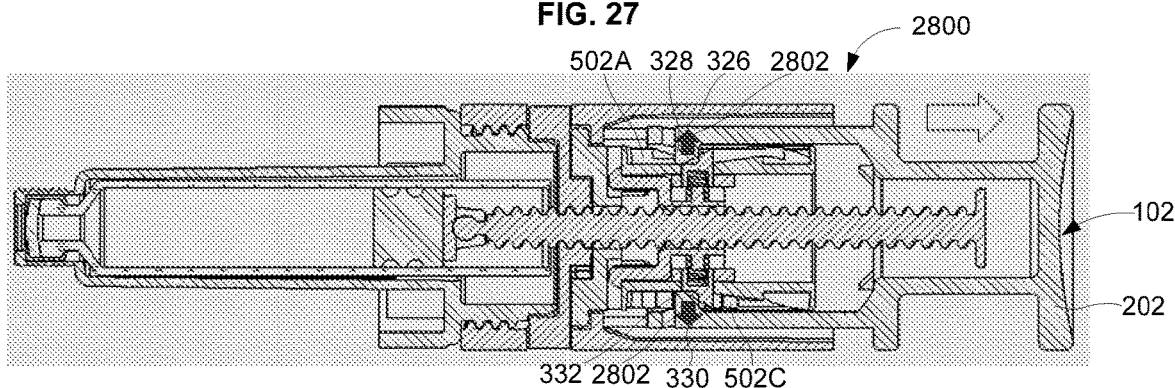
FIG. 28 illustrates another cross sectional view of the dispensing device of FIG. 1 depicting levers of the thumb pad flex up during dose setting.

FIG. 28 illustrates another cross sectional view (2800) of the dispensing device (102) of FIG. 1 depicting the levers (326) and (330) of the thumb pad (202) when flexed up during dose setting, according to one embodiment of the present disclosure. Specifically, during dose setting, the levers (326) and (330) flex up in order to enable the thumb pad (202) to ride on the first and third linear cam profiles (502A) and (502C). The directions in which the levers (326) and (330) flex up during dose setting are indicated using two arrow marks (2802) in FIG. 28.

Figure 29:
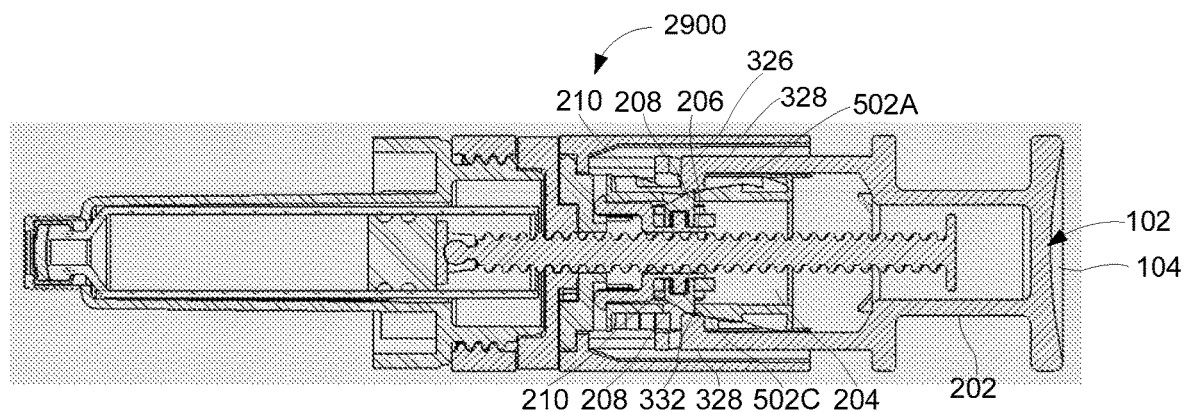
FIG. 29 illustrates another cross sectional view of the dispensing device of FIG. 1 depicting compression of the EOL locks during dose setting.

FIG. 29 illustrates another cross sectional view (2900) of the dispensing device (102) of FIG. 1 depicting compression of the EOL locks (208) while setting dose, according to one embodiment of the present disclosure. As previously noted, when the EOL adapter (206), along with the EOL locks (208) and the EOL compression springs (210), is fitted with the cam drum (204), the EOL locks are configured to protrude out through the slots (511A-D) of the linear cam profiles (502A-D), respectively. FIG. 29 depicts two such EOL locks (208) that protrude out through the slots (511A) and (511C) associated with the first and third linear cam profiles (502A) and (502C), respectively.

When the thumb pad (202) is pulled out in the direction of the proximal end (104), the lever (326) having the pawl (328) rides over the elevated portion (1306) of the EOL lock (208) and pushes the EOL lock (208) downwards. Since, the EOL lock (208) is seated over the EOL compression spring (210), the force exerted by pushing the EOL lock (208) downwards causes the EOL compression spring (210) to undergo compression, as shown in FIG. 29. In addition, the compression of the EOL compression spring (210) ensures the elevated portion (1306) of the EOL lock (208) is protruded into the cam drum (204), thereby providing a path for the lever (326) to move further towards the proximal end (104). It is to be understood that, similarly, the lever (330) having the pawl (332) passes beyond another EOL lock (208) towards the proximal end (104) due to compression of the EOL compression spring (210).

Figure 30:
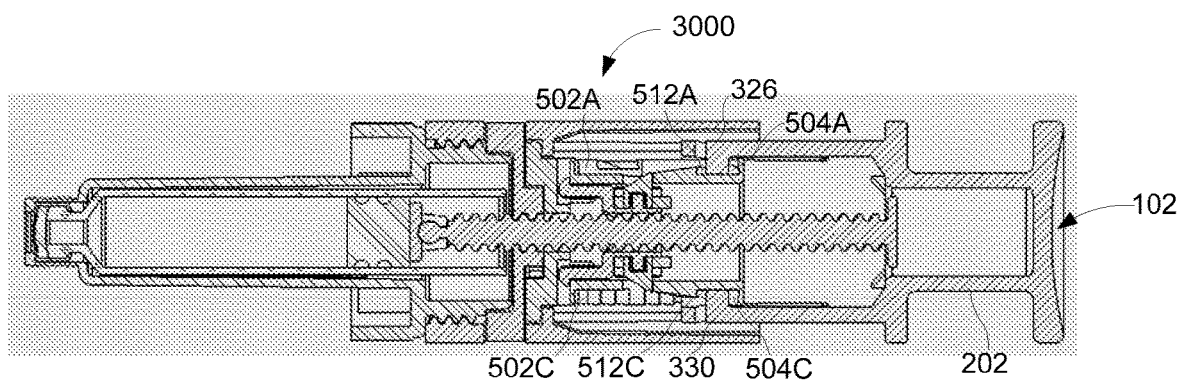
FIG. 30 is a cross sectional view depicting the dispensing device of FIG. 1 at an end of the first dose setting.

FIG. 30 is another cross sectional view (3000) of the dispensing device (102) of FIG. 1 depicting the dispensing device (102) at an end of a first dose setting stage, according to one embodiment of the present disclosure. At the end of the first dose setting stage, the levers (326) and (330) are configured to move along the respective paths defined by the first and third linear cam profiles (502A) and (502C) and be placed in a ready position at start points (512A) and (512C) of the respective helical cam profiles (504A) and (504C) to move along the corresponding helical paths.

Figure 31:
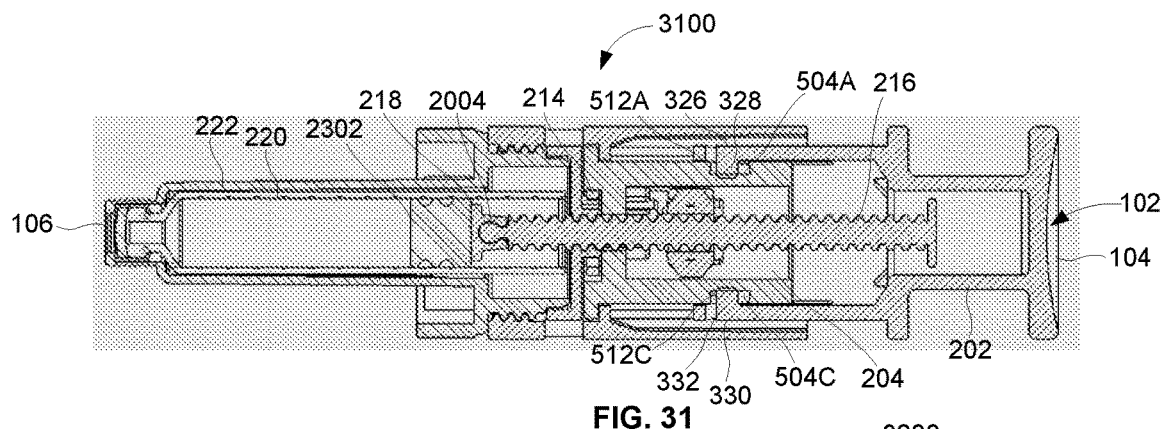
FIG. 31 is another cross sectional view depicting the dispensing device of FIG. 1 placed in a ready position to deliver a first dose.

FIG. 31 is another cross sectional view (3100) of the dispensing device (102) of FIG. 1 depicting the dispensing device (102) placed in a ready position to deliver a first dose, according to one embodiment of the present disclosure. As noted previously with reference to FIG. 30, the levers (326) and (330) are placed in the ready position at the start points (512A) and (512C) of the helical cam profiles (504A) and (504C), respectively. Upon pushing the thumb pad (202) towards the distal end (106), the levers (326) and (330) ride on the paths defined by the helical cam profiles (504A) and (504C), respectively, which leads to rotation of the cam drum (204) in a desired direction (e.g., a clockwise direction) by a designated angle (e.g., by 90°).

Since the lead screw (216) is already secured with the cam drum (204) through the keyway (902), the rotation of the cam drum (204) also rotates the lead screw (216) in the same direction. In one embodiment, the internal threads (1806) of the pawl nut (214) have a pitch that corresponds to a pitch of the lead screw (216). Hence, the pawl nut (214) translates the rotational movement of the lead screw (216) and enables forward movement of the lead screw (216) towards the distal end (106). In addition, the pitch of the lead screw (216) is previously selected such that one rotation of the cam drum (204) by a designated angle leads to movement of the lead screw (216) by a designated distance.

Furthermore, since the universal ball joint (2004) of the lead screw (216) is snap fitted with the push pad (218), the lead screw (216) rotates within the push pad (218) when the cam drum (204) rotates and advances forward along with the push pad (218) by the designated distance. The advancement of the lead screw (216) along with the push pad (218) causes the stopper (2302) to move forward by the designated distance, thus allowing only a designated amount of medicament to be released from the cartridge (220).

Figure 32:
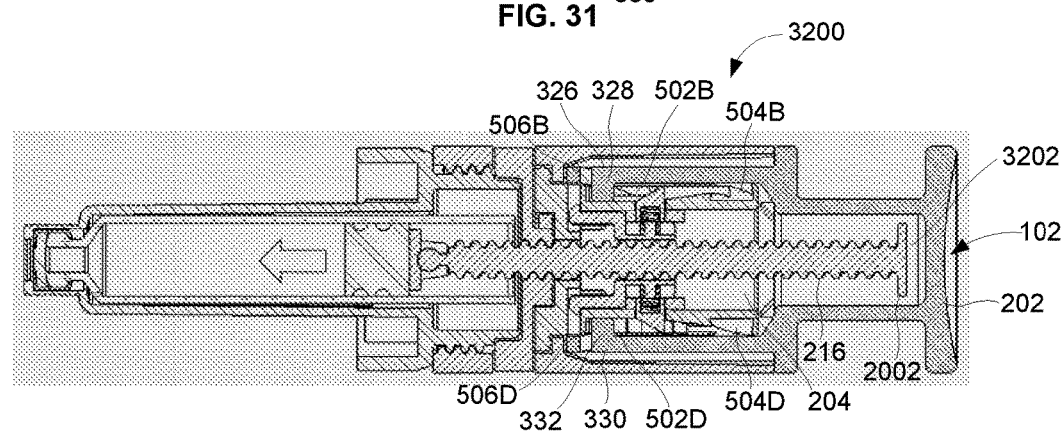
FIG. 32 is another cross sectional view of the dispensing device of FIG. 1 at an end of a first dose delivery stage.

FIG. 32 is another cross sectional view (3200) of the dispensing device (102) of FIG. 1 depicting the dispensing device (102) at an end of a first dose delivery stage, according to one embodiment of the present disclosure. At the end of the first dose delivery stage, the levers (326) and (330) complete the respective paths defined by the first and third helical cam profiles (504A) and (504C) and are placed in ready position at start points (506B) and (506D) of the second and fourth linear cam profiles (502B) and (502D) for a second dose set. In certain embodiments, at the end of the first dose delivery stage, there is a small gap (3202) formed between the flange (2002) of the lead screw (216) and the thumb pad (202). The small gap (3202) corresponds to the designated distance by which the lead screw (216) moved due to rotation of the cam drum (204) during the first dose delivery.

Figure 33:
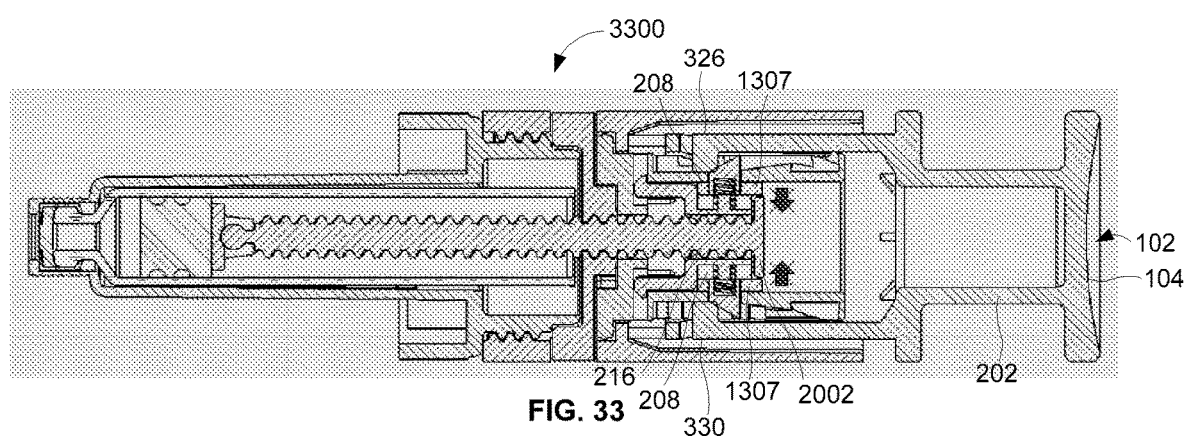
FIG. 33 is another cross sectional view of the dispensing device of FIG. 1 at its end of life.

FIG. 33 is another cross sectional view (3300) of the dispensing device (102) of FIG. 1 depicting the dispensing device (102) at its end of life, according to one embodiment of the present disclosure. As noted previously, at the end of the life cycle of the dispensing device (102), the flange (2002) of the lead screw (216) is configured to be positioned under the EOL locks (208). More specifically, the flange (2002) is placed under the flange-engaging surface (1307) of the EOL locks (208) as shown in FIG. 33. The flange (2002), thus placed under the EOL locks (208), prevents the EOL locks (208) from undergoing compression against the EOL compression springs (210) when the levers (326) and (330) attempt to push the EOL locks (208) downward. Thereby, the EOL locks (208) act as a barrier for the levers (326) and (330) and prevent the thumb pad (202) from moving further towards the proximal end (104). This ensures that the user would not be able to set the dose after the final dose is delivered, and hence, the user is prevented from re-using the dispensing device (102) after its end of life.

Unlike typical dispensing devices in which a user has to keep turning a rotatable head for setting a dose, the dispensing device (102) allows the user to set a dose of a material to be dispensed out seamlessly by simply pulling out the thumb pad (202) towards a proximal end (104) of the dispensing device (102). The dispensing device (102) prevents the user from setting and delivering a wrong dose. The one-way ratchets (510A-D) of the dispensing device (102) allow the thumb pad (202) to move only towards the proximal end (104) of the dispensing device (102). When the user attempts to deliver a dose without setting the dose completely, the thumb pad (202) is locked with the one-way ratchets (510A-D) to avoid delivery of the wrong dose. Further, the EOL adapter (206), the EOL locks (208), and the EOL compression springs (210) of the dispensing device (102) are configured to prevent the user from re-using the dispensing device (102) after a final dose is delivered. Additionally, the dispensing device (102) includes a cam drum (204), which in turn, includes at least one linear cam profile that provide paths for setting a dose and at least one helical cam profile that provide alternative paths for delivering the dose to prevent any dose delivery when setting the dose. The various components of the dispensing device (102) described herein allow the dispensing device (102) to be configured for multiple uses such that the dispensing device (102) dispenses a fixed dose during every dose delivery operation. Alternatively, the dispensing device (102) can be configured to use once as a disposable pen.

Although specific features of various embodiments of the present systems and methods may be shown in and/or described with respect to some drawings and not in others, this is for convenience only. It is to be understood that the described features, structures, and/or characteristics may be combined and/or used interchangeably in any suitable manner in the various embodiments shown in the different figures.

While only certain features of the present systems and methods have been illustrated and described herein, many modifications and changes will occur to those skilled in the art. It is, therefore, to be understood that the appended claims are intended to cover all such modifications and changes as fall within the true spirit of the claimed invention.

We claim:

1. A dispensing device (102), comprising:
   a thumb pad (202) that is configured to be pulled out in a direction away from a distal end (106) of the dispensing device (102) for setting a dose of a material to be dispensed and to be pushed in towards the distal end (106) of the dispensing device (102) for delivering the dose;
   a cam drum (204) that is coupled to the thumb pad (202), wherein the cam drum (204) comprises:
      a distal end that comprises a ratchet (904);
      a plurality of linear cam profiles (502A-D) disposed on a surface of the cam drum (204), wherein the thumb pad (202) is configured to ride on at least one linear cam profile selected from the plurality of linear cam profiles (502A-D) when setting the dose, and
      a plurality of helical cam profiles (504A-D) disposed on the surface of the cam drum (204), wherein the thumb pad (202) is configured to ride on at least one helical cam profile selected from the plurality of helical cam profiles (504A-D) when delivering the dose; and
   a pawl nut (214) comprising a one-way pawl (1804), wherein the one-way pawl (1804) is configured to engage with the ratchet (904) that is disposed at the distal end of the cam drum (204) and is further configured to prevent a rotation of the cam drum (204) in an undesired direction.

2. The dispensing device (102) as claimed in claim 1, wherein each of the plurality of linear cam profiles (502A-D) comprises a corresponding start point (506A-D), a corresponding end point (508A-D), a corresponding one-way ratchet (510A-D) extending between the corresponding start point (506A-D) and the corresponding end point (508A-D), and a corresponding slot (511A-D) that is located in a path corresponding to each of the plurality of linear cam profiles (502A-D), and wherein each of the plurality of helical cam profiles (504A-D) comprises a corresponding start point (512A-D) and a corresponding end point (514A-D).

3. The dispensing device (102) as claimed in claim 2, wherein a first helical cam profile (504A), selected from the plurality of helical cam profiles (504A-D), is located subsequent to the corresponding end point (508A D) (508A) of a first linear cam profile (502A), selected from the plurality of linear cam profiles (502A-D), wherein a second linear cam profile (502B), selected from the plurality of linear cam profiles (502A-D), is located subsequent to the corresponding end point (514A) of the first helical cam profile (504A).

4. The dispensing device (102) as claimed in claim 3, wherein each of the plurality of linear cam profiles (502A-D) defines a gradient path having a slope that gradually increases from the corresponding start point (506A-D) to the corresponding end point (508A-D), and wherein each of the plurality of helical cam profiles (504A-D) defines a gradient path having a slope that gradually increases from the corresponding start point (512A-D) to the corresponding end point (514A D).

5. The dispensing device (102) as claimed in claim 4, wherein the thumb pad (202) comprises:
   a visual indicator (302) that is externally visible when the thumb pad (202) is pulled out in the direction away from the distal end (106) of the dispensing device (102) by a designated distance to indicate completion of a dose setting process;
   an intermediate portion (308) that is a hollow elongated body and a butting surface (312); and
   a circular shaped hollow body (314) having a first extension (320), a second extension (322), and one or more snap locks (318), wherein the first extension (320) and the second extension (322) extend out from the butting surface (312).

6. The dispensing device (102) as claimed in claim 5, wherein the first extension (320) comprises a first lever (326) and a U-shaped slot (324) on a surface of the first extension (320), wherein the second extension (322) comprises a second lever (330) and another U-shaped slot (324) on a surface of the second extension (322), and wherein the first lever (326) comprises a first pawl (328) and the second lever (330) comprises a second pawl (332).

7. The dispensing device (102) as claimed in claim 6, wherein the pawl nut (214) further comprises:
   a plurality of ribs (1802); and
   a slot that comprises a threaded section (1806), wherein the threaded section (1806) comprises a designated pitch.

8. The dispensing device (102) as claimed in claim 7, further comprising a push pad (218) and a lead screw (216), wherein the lead screw (216) comprises a flange (2002), a body that comprises a thread portion (2006), and a universal ball joint (2004) that is configured to be secured to the push pad (218), wherein the thread portion (2006) comprises a designated pitch that corresponds to the designated pitch of the pawl nut (214).

9. The dispensing device (102) as claimed in claim 8, wherein the cam drum (204) further comprises a keyway (902) that is disposed at a proximal end of the cam drum (204), and wherein the lead screw (216) is configured to pass through the keyway (902) and is coupled to the cam drum (204).

10. The dispensing device (102) as claimed in claim 9, wherein at an initial state of the dispensing device (102) before setting a first dose, the thumb pad (202) is coupled to the cam drum (204) such that the first lever (326) having the first pawl (328) is configured to be placed at the corresponding start point (506A) of the first linear cam profile (502A) of the cam drum (204) and the second lever (330) having the second pawl (332) is configured to be placed at the corresponding start point (506C) of a third linear cam profile (502C) selected from the plurality of linear cam profiles (502A-D) of the cam drum (204), wherein the first linear cam profile (502A) that corresponds to the first lever (326) is different from the third linear cam profile (502C) that corresponds to the second lever (330).

11. The dispensing device (102) as claimed in claim 10, wherein the first lever (326) having the first pawl (328) is configured to move linearly from the corresponding start point (506A) of the first linear cam profile (502A) and to ride on the corresponding one-way ratchet (510A) of the first linear cam profile (502A), and simultaneously, the second lever (330) having the second pawl (332) is configured to move linearly from the corresponding start point (506C) of the third linear cam profile (502C) and to ride on the corresponding one-way ratchet (510C) of the third linear cam profile (502C) when the dose is set by pulling out the thumb pad (202) in the direction away from the distal end (106) of the dispensing device (102).

12. The dispensing device (102) as claimed in claim 11, wherein the first pawl (328) is configured to be locked with the corresponding one-way ratchet (510A) of the first linear cam profile (502A) and the second pawl (332) is configured to be locked with the corresponding one-way ratchet (510C) of the third linear cam profile (502C), and thereby prevent a linear motion of the thumb pad (202) towards the distal end (106) of the dispensing device (102) when delivery of the dose is attempted by pulling out the thumb pad (202) by less than the designated distance in the direction away from the distal end (106) of the dispensing device (102).

13. The dispensing device (102) as claimed in claim 11, wherein the first lever (326) is configured to complete the gradient path defined by the first linear cam profile (502A) and be placed at a ready position at the corresponding start point (512A) of the first helical cam profile (504A), and simultaneously, the second lever (330) is configured to complete the gradient path defined by the third linear cam profile (502C) and be placed at a ready position at the corresponding start point (512C) of a third helical cam profile (504C) selected from the plurality of helical cam profiles (504A-D) at an end of a dose setting stage, wherein the first helical cam profile (504A) on which the first lever (326) is positioned is different from the third helical cam profile (504C) on which the second lever (330) is positioned.

14. The dispensing device (102) as claimed in claim 13, wherein the first lever (326) is configured to ride on the gradient path defined by the first helical cam profile (504A) and the second lever (330) is configured to ride on the gradient path defined by the third helical cam profile (504C) when the dose is delivered by pushing the thumb pad (202) linearly towards the distal end (106) of the dispensing device (102) after the dose is set by pulling out the thumb pad (202) by the designated distance.

15. The dispensing device (102) as claimed in claim 14, wherein the first lever (326) and the second lever (330) are configured to push and rotate the cam drum (204) in a desired direction when the first lever (326) rides on the first helical cam profile (504A) and the second lever (330) rides on the third helical cam profile (504C), thereby converting a linear motion of the thumb pad (202) towards the distal end (106) of the dispensing device (102) into a circular motion of the cam drum (204) in the desired direction.

16. The dispensing device (102) as claimed in claim 15, wherein the cam drum (204) is configured to complete one rotation at a desired angle in the desired direction when the first lever (326) completes the gradient path defined by the first helical cam profile (504A) and the second lever (330) completes the gradient path defined by the third helical cam profile (504C).

17. The dispensing device (102) as claimed in claim 16, wherein the lead screw (216) is configured to rotate along with the cam drum (204) in the desired direction as the lead screw (216) is locked with the cam drum (204) through the keyway (902) when delivering the dose.

18. The dispensing device (102) as claimed in claim 17, wherein the designated pitch associated with the lead screw (216) corresponds to the designated pitch associated with the threaded section (1806) of the pawl nut (214), thereby configuring the pawl nut (214) to convert a circular motion of the lead screw (216) into a linear motion towards the distal end (106) of the dispensing device (102) by a desired distance, and wherein the lead screw (216) that is moved by the desired distance pushes a stopper (2302) within a cartridge (220) to dispense the dose from the cartridge (220).

19. The dispensing device (102) as claimed in claim 18, wherein a length of the lead screw (216) is selected such that when the cam drum (204) completes one rotation, the lead screw (216) is configured to rotate and move by a distance that causes an entire dose accommodated within the cartridge (220) to dispense out in a single dose delivery operation.

20. The dispensing device (102) as claimed in claim 18, wherein the dispensing device (102) is configured to deliver a fixed dose during every single dose delivery operation of the dispensing device (102).

21. The dispensing device (102) as claimed in claim 20, wherein the first lever (326) is configured to ride on the gradient path defined by the first helical cam profile (504A) and the second lever (330) is configured to ride on the gradient path defined by the third helical cam profile (504C) to rotate the cam drum (204) by a designated angle, and thereby configuring the lead screw (216) to rotate and move further from a current position every time by a same distance to dispense the fixed dose during every dose delivery operation.

22. The dispensing device (102) as claimed in claim 21, wherein the cam drum (204) further comprises a barrel engaging surface (905) and a plurality of guide ribs (1002, 1004), wherein the plurality of guide ribs (1002, 1004) are configured to guide the lead screw (216) to pass through the keyway (902) when the cam drum (204) rotates during delivering the dose.

23. The dispensing device (102) as claimed in claim 22, further comprising a pen barrel (212) that acts as an outer body component that is coupled to the butting surface (312) of the thumb pad (202), wherein the pen barrel (212) comprises:

a circular rib (1728) secured to the barrel engaging surface (905) of the cam drum (204) so as to prevent a linear motion of the cam drum (204) towards a proximal end (104) of the dispensing device (102) when setting the dose, and prevent a linear motion of the cam drum (204) towards the distal end (106) of the dispensing device (102) when delivering the dose;

a plurality of semi-circular ribs (1752, 1754), wherein each of the semi-circular ribs (1752, 1754) is configured to be locked with the thumb pad (202) to prevent the thumb pad (202) from moving further in the direction away from the distal end (106) of the dispensing device (102) when the thumb pad (202) is pulled out in the direction away from the distal end (106) of the dispensing device (102) by the designated distance;

a plurality of depressions (1762) disposed at inner surfaces of the pen barrel (212) to provide adequate spaces for the first lever (326) and the second lever (330) to flex up and down and to ride smoothly on the plurality of linear cam profiles (502A-D) and the plurality of helical cam profiles (504A-D) of the cam drum (204);

a plurality of slots (1710, 1712, 1718, 1724) disposed on an outer surface of the pen barrel (212), wherein each of the plurality of slots (1710, 1712, 1718, 1724) is configured to receive and accommodate a rib selected from the plurality of ribs (1802) of the pawl nut (214) such that the pawl nut (214) is placed in a locked condition with respect to the pen barrel (212); and a first pair of guiding surfaces (1758) and a second pair of guiding surfaces (1760), wherein the first extension (320) of the thumb pad (202) fits within and engages against the first pair of guiding surfaces (1758), and wherein the second extension (322) of the thumb pad (202) fits within and engages against the second pair of guiding surfaces (1760).

24. The dispensing device (102) as claimed in claim 23, wherein the first pair of guiding surfaces (1758) and the second pair of guiding surfaces (1760) guide the first extension (320) and the second extension (322), respectively, in a linear fashion in order to move the thumb pad (202) linearly without undergoing a circulatory motion when the thumb pad (202) is pulled out in the direction away from the distal end (106) of the dispensing device (102) or when the thumb pad (202) is pushed in towards the distal end (106) of the dispensing device (102).

25. The dispensing device (102) as claimed in claim 8, wherein the lead screw (216) is placed at a first position within the thumb pad (202) at an initial state of the dispensing device (102), wherein the dispensing device (102) further comprises:

a plurality of end of life (EOL) locks (208), wherein each of the plurality of EOL locks (208) comprises an elastic member seating surface (1312), a flange-engaging portion (1307), and an elevated portion (1306); and an end of life (EOL) adapter (206) that acts as a carrier of the plurality of EOL locks (208) and is coupled to the cam drum (204), wherein the flange (2002) of the lead screw (216) is configured to be positioned below the flange-engaging portion (1307) of at least one EOL lock selected from the plurality of EOL locks (208) that prevent the thumb pad (202) from moving further in the direction away from the distal end (106) of the dispensing device (102) to prevent further setting of the dose after a final dose is delivered.

26. The dispensing device (102) as claimed in claim 25, wherein the EOL adapter (206) comprises a plurality of portions and at least one snap lock feature (1218, 1220) for locking the EOL adapter (206) with the cam drum (204), wherein each of the plurality of portions of the EOL adapter (206) comprises a first flexure (1222A), a second flexure (1224A), an EOL lock seating surface (1228A) that is disposed between the first flexure (1222A) and the second flexure (1224A), and a peg (1226A) that protrudes out from the EOL lock seating surface (1228A).

27. The dispensing device (102) as claimed in claim 26, further comprising a plurality of elastic members (210), wherein the peg (1226A) associated with the EOL adapter (206) supports an elastic member (210) selected from the plurality of elastic members (210), and wherein a particular EOL lock selected from the plurality of EOL locks (208) is coupled to a particular portion selected from the plurality of portions of the EOL adapter (206) by seating the elastic member seating surface (1312) corresponding to the particular EOL lock on the elastic member (210) that is supported by the peg (1226A) associated with the particular portion of the EOL adapter (206).

28. The dispensing device (102) as claimed in claim 27, wherein the EOL adapter (206) along with the plurality of EOL locks (208) are placed within the cam drum (204) and are locked with the cam drum (204) using the at least one snap lock feature (1218, 1220), such that, the elevated portion (1306) associated with each of the plurality of EOL locks (208) protrudes out through the corresponding slot (511A-D) disposed along one or more paths a path defined by each of the plurality of linear cam profiles (502A-D) of the cam drum (204).

29. The dispensing device (102) as claimed in claim 28, wherein the first pawl (328) and the second pawl (332) associated with the thumb pad (202) ride over the plurality of linear cam profiles (502A-D) and compress the elevated portion (1306) associated with the at least one EOL lock selected from the plurality of EOL locks (208) within the cam drum (204) to move further and complete the dose setting process when the dose is set by pulling out the thumb pad (202) proximal end (104) in the direction away from the distal end (106) of the dispensing device (102).

30. The dispensing device (102) as claimed in claim 29, wherein the flange (2002) of the lead screw (216) is configured to be positioned within the cam drum (204) and below the flange-engaging portion (1307) associated with the at least one EOL lock selected from the plurality of EOL locks (208) after the final dose is delivered, and wherein the elevated portion (1306) associated with the at least one EOL lock selected from the plurality of EOL locks (208) is prevented from undergoing compression within the cam drum (204) due to the presence of the flange (2002) causing a block in a path of the thumb pad (202) to prevent setting of another dose subsequent to delivery of the final dose.

* * * * *